(12) United States Patent
Gordon et al.

(10) Patent No.: US 6,673,927 B2
(45) Date of Patent: *Jan. 6, 2004

(54) FARNESYL TRANSFERASE INHIBITORS

(75) Inventors: Thomas D. Gordon, Medway, MA (US); Barry A. Morgan, Franklin, MA (US)

(73) Assignee: Societe de Conseils de Recherches et d'Applications Scientifiques, S.A.S., Paris (FR)

(*) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 08/752,546

(22) Filed: Nov. 20, 1996

(65) Prior Publication Data

US 2002/0013319 A1 Jan. 31, 2002

Related U.S. Application Data

(60) Provisional application No. 60/049,997, filed on Feb. 16, 1996.

(51) Int. Cl.$^7$ ................... C07D 487/04; A61K 31/4985

(52) U.S. Cl. ................. 544/350; 514/249; 514/250; 514/365; 514/374; 514/400; 544/346; 548/203; 548/204; 548/205; 548/335.5; 548/338.1; 548/235; 548/236

(58) Field of Search .................. 544/350; 514/249

(56) References Cited

U.S. PATENT DOCUMENTS

5,229,386 A  7/1993  Takasugi et al. .......... 514/236.8

FOREIGN PATENT DOCUMENTS

| WO | WO 94/26723 | 11/1994 |
| WO | WO 95/00497 | 1/1995 |
| WO | WO 97/19075 | 5/1997 |

OTHER PUBLICATIONS

Kitosravi–Far et al, Cell Growth & Differentiation vol. 3, p. 461–469, 1992.*
Bhide et al., "Rational Design of Potent Carboxylic Acid Based Bisubstrate Inhibitors of Ras Farnesyl Protein Transferase", Bioorganic & Medicinal Chemistry Letters, 4:2107–2112, 1994.
Bishop et al., "Novel Tricyclic Inhibitors of Farnesyl Protein Transferase", The Journal of Biological Chemistry, 270:30611–30618, 1995.
Buss et al., "Farnesyl Transferase Inhibitors: the Successes and Surprises of a New Class of Potential Cancer Chemotherapeutics", Chemistry & Biology, 2:787–791, 1995.

Clerc et al., "Constrained Analogs of KCVFM with Improved Inhibitory Properties Against Farnesyl Transferase" Bioorganic & Medicinal Chemistry Letters, 5:1779–1784, 1995.
deSolms et al., "Pseudodipeptide Inhibitors of Protein Farnesyltransferase", J. Med. Chem., 38:3967–3971, 1995.
Garcia et al., "Peptidomimetic Inhibitors of Ras Farnesylation and Function in Whole Cells", The Journal of Biological Chemistry, 268:18415–18418, 1993.
Gibbs et al., "Farnesyltransferase Inhibitors: Ras Research Yields a Potential Cancer Therapeutic", Cell, 77:175–178, 1994.
Graham et al., "Pseudopeptide Inhibitors of Ras Farnesyl–Protein Transferase", J. Med. Chem. 37:725–732, 1994.
Harrington et al., "Cysteine and Methionine Linked by Carbon Pseudopeptides Inhibit Farnesyl Transferase", Bioorganic & Medicinal Chemistry Letters, 4:2775–2780, 1994.
Hunt et al., "Potent, Cell Active, Non–Thiol Tetrapeptide Inhibitors of Farnesyltransferase", J. Med. Chem. 39:353–358, 1996.
James et al., "Benzodiazepine Peptidomimetics: Potent Inhibitors of Ras Farnesylation in Animal Cells", Science, 260:1937–1942, 1993.
James et al., "Polylysine and CVIM Sequences of K–RasB Dictate Specificity of Prenylation and Confer Resistance to Benzodiazepine Peptidomimetic in Vitro", The Journal of Biological Chem., 270:6221–6226, 1995.
Koblan et al., "NMR Studies of Novel Inhibitors Bound to Farnesyl–Protein Transferase", Protein Science, 4:681–688, 1995.

(List continued on next page.)

*Primary Examiner*—Emily Bernhardt
(74) *Attorney, Agent, or Firm*—Fish & Richardson; Brian R. Morrill; Alan F. Feeney

(57) ABSTRACT

The present invention is directed to compounds of the

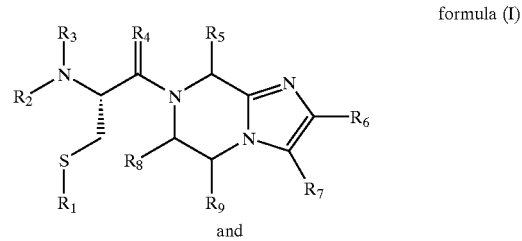

formula (I)

and

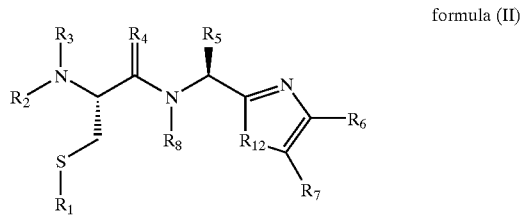

formula (II)

wherein the variables are as defined in the specification. The compounds are useful for inhibiting farnesyl transferase and for the treatment of tumors and restenosis.

4 Claims, No Drawings

OTHER PUBLICATIONS

Kohl et al., "Development of Inhibitors of Protein Farnesylation as Potential Chemotherapeutic Agents", Journal of Cellular Biochemistry, 22:145–150, 1995.

Kohl et al., "Inhibition of Farnesyltransferase Induces Regression of Mammary and Salivary Carcinomas in Ras Transgenic Mice", Nature Medicine, 1:792–797, 1995.

Kohl et al., "Inhibition of Ras Function in Vitro and In Vivo Using Inhibitors of Farnesyl–Protein Transferase", Methods in Enzymology, 255:378–386, 1995.

Kohl et al., "Selective Inhibition of ras–Dependent Transformation by a Farnesyltransferase Inhibitor", Science, 260:1934–1937. 1993.

Leftheris et al., "Development of Highly Potent Inhibitors of Ras Farnesyltransferase Possessing Cellular and in Vivo Activity", J. Med. Chem., 39:224–236, 1996.

Lerner et al., "Ras CAAX Peptidomimetic FTI–277 Selectively Blocks Oncogenic Ras Signaling by Inducing Cytoplasmic Accumulation of Inactive Ras–Raf Complexes", The J. of Biological Chem., 270:26802–26806, 1995.

Nagasu et al., "Inhibition of Human Tumor Xenograft Growth by Treatment with the Farnesyl Transferase Inhibitor B956", Cancer Research, 55:5310–5314, 1995.

Nigam et al., "Potent Inhibition of Human Tumor $p21^{ras}$ Farnesyltransferase by $A_1A_2$–Lacking $p21^{ras}$ $CA_1A_2X$ Peptidometrics", The Journal of Biological Chemistry, 268:20695–20698, 1993.

Patel et al., "Phenol Based Tripeptide Inhibitors of Ras Farnesyl Protein Transferase", Bioorganic & Medicinal Chemistry Letters, 4:1883–1888, 1994.

Qian et al., "Design and Synthesis of Non–Peptide Ras CAAX Mimetics as Potent Farnesyltransferase Inhibitors", J. Med. Chem., 39:217–223, 1996.

Qian et al., "Design and Structural Requirements of Potent Peptidomimetic Inhibitors of $p21^{ras}$ Farnesyltransferase", The Journal of Biological Chemistry, 269:12410–12413, 1994.

Reiss et al., "Sequence Requirement for Peptide Recognition by Rat Brain $p21^{ras}$ Protein Farnesyltransferase", Proc. Natl. Acad. Sci., 88:732–736, 1991.

Sepp–Lorenzino et al., "A Peptidomimetic Inhibitor of Farnesyl: Protein Transferase Blocks the Anchorage–Dependent and –Independent Growth of Human Tumor Cell Lines", Cancer Research, 55:5302–5309, 1995.

Singh et al., "Fusidienol: A Novel Inhibitor of Ras Farnesyl–Protein Transferase from Fusidium Griseum", Pergamon Tetrahedron Letters, 35:4693–4696, 1994.

Vogt et al., "A Non–Peptide Mimetic of Ras–CAAX: Selective Inhibition of Farnesyltransferase and Ras Processing", The Journal of Biological Chemistry, 270:660–664, 1995.

Williams et al., "2–Substituted Piperazines as Constrained Amino Acids. Application to the Synthesis of Potent, Non Carboxylic Acid Inhibitors of Farnesyltransferase", J. Med. Chem., 39:1345–1348, 1996.

* cited by examiner

FARNESYL TRANSFERASE INHIBITORS

CROSS REFERENCE TO RELATED APPLICATIONS

This application claims the benefit of U.S. Provisional Application Ser. No. 60/049,997 filed Feb. 16, 1996.

BACKGROUND OF THE INVENTION

Ras is a 21,000 molecular weight protein important in the signal transduction pathway for normal cell growth. The protein is produced in the ribosome, released into the cytosol, and post-translationally modified. The first step in the series of post-translational modifications is the alkylation of $Cys^{168}$ with farnesyl pyrophosphate in a reaction catalyzed by the enzyme farnesyl transferase (Hancock, J F, et al., Cell 57:1167–1177 (1989)). Subsequently, the three C-terminal amino acids are cleaved (Gutierrez, L, et al., EMBO J. 8:1093–1098 (1989)), and the terminal $Cys^{168}$ is methyl esterified (Clark, S, et al., Proc. Nat'l Acad. Sci. (USA) 85:4643–4647 (1988)). Some forms of Ras are also reversibly palmitoylated on cysteine residues immediately N-terminal to $Cys^{168}$ (Buss, J E, et al., Mol. Cell. Biol. 6:116–122 (1986)). These modifications increase the hydrophobicity of the C-terminal region of Ras, causing it to localize at the surface of the cell membrane. Localization of Ras to the cell membrane is necessary for normal function (Willumsen, B M, et al., Science 310:583–586 (1984)).

Oncogenic forms of Ras are observed in a relatively large number of cancers including over 50 percent of colon cancers, over 30 percent of lung cancers, and over 90 percent of pancreatic cancers (Bos, J L, Cancer Research 49:4682–4689 (1989)). These observations suggest that intervention in the function of Ras mediated signal transduction may be useful in the treatment of cancer.

Previously, it has been shown that the C-terminal tetrapeptide of Ras has the "CAAX" motif (wherein C is cysteine, A is an aliphatic amino acid, and X is any amino acid). Tetrapeptides having this structure have been shown to be inhibitors of farnesyl transferase (Reiss, et al., Cell 62:81–88 (1990)). Poor potency of these early farnesyl transferase inhibitors has prompted the search for new inhibitors with more favorable pharmacokinetic behavior (James, G L, et al., Science 260:1937–1942 (1993); Kohl, N E, et al., Proc. Nat'l Acad. Sci. (USA) 91:9141–9145 (1994); deSolms, S J, et al., J. Med. Chem. 38:3967–3971 (1995); Nagasu, T, et al., Cancer Research 55:5310–5314 (1995); Lerner, E C, et al., J. Biol. Chem. 270:26802–26806 (1995)).

Recently, it has been shown that a farnesyl transferase inhibitor will block growth of Ras-dependent tumors in nude mice (Kohl, N E, et al., Proc. Nat'l Acad. Sci. (USA) 91:9141–9145 (1994)). In addition, it has been shown that over 70 percent of a large sampling of tumor cell lines are inhibited by farnesyl transferase inhibitors with selectivity over non-transformed epithelial cells (Sepp-Lorenzino, I, et al., Cancer Research, 55:5302–5309 (1995)).

SUMMARY OF THE INVENTION

In one aspect, the invention features a compound having the formula (I) or formula (II):

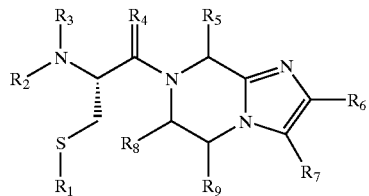

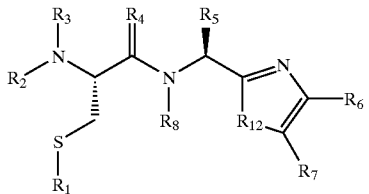

wherein:
$R_1$ is H, lower alkyl, cycloalkylthio, or lower alkylthio, or, together with $R_2$, form —$CH_2$— or —$C(CH_3)_2$—;
each of $R_2$ and $R_3$, independently, is H, lower alkyl, and cycloalkyl;
$R_4$ is $H_2$ or O;
$R_5$ is H, or substituted or unsubstituted lower alkyl, lower alkenyl, lower alkynyl, cycloalkyl, cycloalkyl lower alkyl, cycloalkenyl, cycloalkenyl lower alkyl, aryl, aryl lower alkyl, heterocyclyl, or heterocyclyl lower alkyl, wherein the substituent is lower alkyl, —O—$R_{10}$, —S(O)$_m R_{10}$ (where m is 0, 1, or 2), —N($R_{10}$)($R_{11}$), —N—C(O)—$R_{10}$, —NH—($SO_2$)—$R_{10}$; —$CO_2$—$R_{10}$, —C(O)—N($R_{10}$)($R_{11}$), or —($SO_2$)—N($R_{10}$)($R_{11}$);
each of $R_6$ and $R_7$, independently, is H, —C(O)—NHCH$R_{13}CO_2R_{14}$, or substituted or unsubstituted lower alkyl, cycloalkyl, cycloalkyl lower alkyl, cycloalkenyl, cycloalkenyl lower alkyl, aryl, aryl lower alkyl, heterocyclyl, or heterocyclyl lower alkyl, wherein the substituent is OH, lower alkyl, lower alkoxy, aryloxy, aryl lower alkoxy, —N($R_{10}$)($R_{11}$), —COOH, —CON($R_{10}$)($R_{11}$), or halo, or $R_6$ and $R_7$, together, form aryl or heterocyclyl;
each of $R_8$ and $R_9$, independently, is H, or substituted or unsubstituted lower alkyl, cycloalkyl, cycloalkyl lower alkyl, cycloalkenyl, cycloalkenyl lower alkyl, aryl, aryl lower alkyl, heterocyclyl, or heterocyclyl lower alkyl, wherein the substituent is OH, lower alkyl, lower alkoxy, —N($R_{10}$)($R_{11}$), COOH, —C(O)N—($R_{10}$)($R_{11}$), or halo, or $R_8$ and $R_9$, together, form aryl or heterocyclyl;
each of $R_{10}$ and $R_{11}$, independently, is H, lower alkyl, aryl, aryl lower alkyl, cycloalkyl, cycloalkyl lower alkyl, heterocyclyl, or heterocyclyl lower alkyl;
$R_{12}$ is $NR_9$, S, or O;
$R_{13}$ is substituted or unsubstituted lower alkyl wherein the substituent is lower alkyl, —$OR_{10}$, —S(O)$_m R_{10}$ (wherein m is 0, 1, or 2) or —N($R_{10}$)($R_{11}$); and
$R_{14}$ is H or lower alkyl; or
a pharmaceutically acceptable salt thereof.
Examples of the present invention include the following:
7-(2-amino-1-oxo-3-thio-propyl)-8-butyl-2-phenyl-5,6,7, 8-tetrahydro-imidazo-[1,2a]-pyrazine (Compound 1);
7-(2-amino-1-oxo-3-thio-propyl)-8-butyl-2-(4-fluorophenyl)-5,6,7,8-tetrahydro-imidazo-[1,2a]-pyrazine (Compound 2);

7-(2-amino-1-oxo-3-thio-propyl)-8-butyl-2-(2-methoxyphenyl)-5,6,7,8-tetrahydro-imidazo-[1,2a]-pyrazine (Compound 3);

7-(2-amino-1-oxo-3-thio-propyl)-8-butyl-2-(3-methoxyphenyl)-5,6,7,8-tetrahydro-imidazo-[1,2a]-pyrazine Compound 4);

7-(2-amino-1-oxo-3-thio-propyl)-8-butyl-2-(4-methoxyphenyl)-5,6,7,8-tetrahydro-imidazo-[1,2a]-pyrazine Compound 5);

7-(2-amino-1-oxo-3-thio-propyl)-8-(2-hydroxy-ethyl)-2-phenyl-5,6,7,8-tetrahydro-imidazo-[1,2a]-pyrazine (Compound 6);

7-(2-amino-3-thio-propyl)-8-butyl-3-phenyl-5,6,7,8-tetrahydro-imidazo-[1,2a]-pyrazine (Compound 7);

2-(1-(N-(2-amino-1-oxo-3-thiopropyl)-N-methyl)-amino-pentyl)-5-phenyl-imidazole (Compound 8);

2-(((2-amino-1-oxo-3-mercapto-propyl)-amino)-methyl)-5-phenyl-thiazole-4-carbonyl-methionine (Compound 9);

7-(2-amino-1-oxo-3-thio-propyl)-2-(2-methoxyphenyl)-8-(2-methylpropyl)-5,6,7,8-tetrahydro-imidazol[1,2a]pyrazine (Compound 11);

7-(2-amino-1-oxo-3-thio-propyl)-8-butyl-2-(2-ethoxyphenyl)-5,6,7,8-tetrahydro-imidazo-[1,2a]-pyrazine (Compound 13);

7-(2-amino-1-oxo-3-thio-propyl)-8-butyl-2-(2-hydroxyphenyl)-5,6,7,8-tetrahydro-imidazo-[1,2a]-pyrazine (Compound 14);

2-(1-(N-(2-amino-1-oxo-3-thiopropyl)-N-methyl)-amino-pentyl-5-(2-methoxyphenyl)-imidazole (Compound 15);

7-(2-amino-1-oxo-3-thiopropyl)-8-(2-methylpropyl)-2-(1-naphthyl)-5,6,7,8-tetrahydroimidazo[1,2a]pyrazine (Compound 17);

7-(2-amino-1-oxo-3-thiopropyl)-8-(1-methylpropyl)-2-(2-methoxyphenyl)-5,6,7,8-tetrahydroimidazo[1,2a]pyrazine (Compound 18);

S-(dimethylethyl)-s'-[2-amino-3-oxo-3(8-butyl-2-(2-methoxyphenyl;)-5,6,7,8-tetrahydroimidazo[1,2a]pyrazine-7-yl)propyl]disulfide (Compound 21);

7-(2-amino-1-oxo-3-thiopropyl)-8-butyl-2-(2-methylphenyl)-5,6,7,8-tetrahydroimidazo[1,2a]pyrazine (Compound 22);

7-(2-amino-1-oxo-3-thiopropyl)-8-(1,1-dimethylethyl)-2-(2-methoxyphenyl)-5,6,7,8-tetrahydroimidazo[1,2a]pyrazine (Compound 24);

7-(2-amino-1-oxo-3-thiopropyl)-8-(1-methylpropyl)-2-(2-(phenylmethoxy)phenyl)-5,6,7,8-tetrahydroimidazo[1,2a]pyrazine (Compound 25);

7-(2-amino-1-oxo-3-thiopropyl)-8-(cyclohexylmethyl)-2-(2-methoxyphenyl)-5,6,7,8-tetrahydroimidazo[1,2a]pyrazine (Compound 26);

7-(2-amino-1-oxo-3-thiopropyl)-2-(2-methoxyphenyl)-8-(1-methylethyl)-5,6,7,8-tetrahydroimidazo[1,2a]]pyrazine (Compound 27);

7-(2-amino-1-oxo-3-thiopropyl)-8-butyl-2(2-hydroxy-6-methoxyphenyl)-5,6,7,8-tetrahydro[1,2a]pyrazine (Compound 29);

2-(2-methoxyphenyl)-8-(1-methylpropyl)-5,6,7,8-tetrahydro-7-((thiazolidin-4-yl)carbonyl)-imidazo[1,2a]pyrazine (Compound 31);

7-(2-amino-1-oxo-3-thiopropyl)-3-bromo-8-butyl-2-(2-methoxyphenyl)-5,6,7,8-tetrahydro-imidazo[1,2a]pyrazine (Compound 32);

7-(2-amino-1-oxo-3-thiopropyl)-8-butyl-2,3-diphenyl-5,6,7,8-tetrahydroimidazo-[1,2a]pyrazine (Compound 34);

7-(2-amino-1-oxo-3-thiopropyl)-3-bromo-8-butyl-2-phenyl-5,6,7,8-tetrahydro-imidazo[1,2a]pyrazine (Compound 36);

7-(2-amino-1-oxo-3-thiopropyl)-2-cyclohexyl-8-(cyclohexylmethyl)-5,6,7,8-tetrahydro-imidazo[1,2a]pyrazine (Compound 37);

7-(2-amino-1-oxo-3-thiopropyl)-8-hexyl-2-(2-methoxyphenyl)-5,6,7,8-tetrahydro-imidazo[1,2a]pyrazine (Compound 42);

7-(2-amino-1-oxo-3-thiopropyl)-8-(cyclohexylethyl)-2-(2-methoxyphenyl)-5,6,7,8-tetrahydroimidazo[1,2a]pyrazine (Compound 44);

7-(2-amino-1-oxo-3-thiopropyl)-8-(cyclohexyl)-2-(2-methoxyphenyl)-5,6,7,8-tetrahydroimidazo[1,2a]pyrazine (Compound 46);

7-(2-amino-1-oxo-3-thiopropyl)-8-(2-(4-methoxycyclohexyl)-methyl)-2-(2-methoxyphenyl)-5,6,7,8-tetrahydroimidazo[1,2a]pyrazine (Compound 47);

7-(2-amino-1-oxo-3-thiopropyl)-8-(cyclohexylmethyl)-2-phenyl)-5,6,7,8-tetrahydroimidazo[1,2a]pyrazine (Compound 49);

7-(2-amino-1-oxo-3-thiopropyl)-8-(4-methoxycyclohexyl)-2-(2-methoxyphenyl)-5,6,7,8-tetrahydroimidazo[1,2a]pyrazine (Compound 51);

[S-[2-amino-3-oxo-3-(8-cyclohexylmethyl)-2-(2-methoxyphenyl)-5,6,7,8-tetrahydro-imidazo[1,2a]pyrazine-7-yl)-propyl]-S'-cyclohexyl]disulfide (Compound 52);

7-(2-amino-1-oxo-3-thiopropyl)-8-(4-methoxycyclohexyl)methyl-2-(2-methoxyphenyl)-5,6,7,8-terahydroimidazo[1,2a]pyrazine (cis isomer) (Compound 53);

7-(2-amino-1-oxo-3-thiopropyl)-2-(2-methoxyphenyl)-8-(4-piperidinylmethyl)-5,6,7,8-terahydroimidazo[1,2a]pyrazine (Compound 54);

7-(2-amino-1-oxo-3-thiopropyl)-2-(2-methoxyphenyl)-8-(2-piperidinylmethyl)-5,6,7,8-terahydroimidazo[1,2a]pyrazine (Compound 55);

7-(2-amino-1-oxo-3-thiopropyl)-2-(2-methoxyphenyl)-8-(3-piperidinylmethyl)-5,6,7,8-terahydroimidazo[1,2a]pyrazine (Compound 56);

7-(2-amino-1-oxo-3-thiopropyl)-8-(cyclohexylmethyl)-2-(1-naphthyl)-5,6,7,8-tetrahydroimidazo[1,2a]pyrazine (Compound 57);

[S-[2-amino-3-oxo-3-(8-cyclohexylmethyl)-2-(2-methoxyphenyl)-5,6,7,8-tetrahydro-imidazo[1,2a]pyrazin-7-yl)-propyl]-S'-ethyl]disulfide (Compound 58);

7-(2-amino-1-oxo-3-thiopropyl)-2-(2-methoxyphenyl)-8-(2-methylthio)-ethyl-5,6,7,8-tetrahydroimidazo[1,2a]pyrazine (Compound 59);

7-(2-amino-1-oxo-3-thiopropyl)-8-(3-indolinylmethyl)-2-(2-methoxyphenyl)-8-5,6,7,8-tetrahydroimidazo[1,2a]pyrazine (Compound 60); and 7-(2-amino-1-oxo-3-thiopropyl)-8-(1-methylimidazol-3-yl)methyl-2-(2-methoxyphenyl)-8-5,6,7,8-tetrahydroimidazo[1,2a]pyrazine (Compound 61).

In another aspect, the invention features a dimeric compound made of two identical or different compounds (monomers) as described above, or a pharmaceutically acceptable salt thereof. The monomers are linked to each other to form the dimer via a disulfide bond. More specifically, $R_1$ in the first monomer and $R_1$ in the second monomer, in combination, form a disulfide bond.

Examples of dimers of the invention include:

bis-1,1'-[2-amino-3-(8-butyl-2-(2-methoxyphenyl)-5,6,7,8-tetrahydro-imidazo[1,2a]piperazine-7-yl)-3-oxo]propyl disulfide (Compound 10);

bis-1,1'-[2-amino-3-(2-(2-methoxyphenyl)-8-(2-methylpropyl)-5,6,7,8-tetrahydro-imidazo[1,2a]piperazine-7-yl)-3-oxo]propyl disulfide (Compound 12);

bis-1,1'-[2-(1-(N-(2-amino-1-oxo-3-thiopropyl)-N-methylamino)-pentyl]-5-(2-methoxyphenyl)imidazole]disulfide (Compound 16);

bis-1,1'-7-(2-amino-1-oxo-3-thiopropyl-(2-(1-naphthyl)-8-(2-methylpropyl)-5,6,7,8-tetrahydroimidazo[1,2a]pyrazin-7-yl)disulfide (Compound 19).

bis-1,1'-[7-(2-amino-1-oxo-3-thiopropyl)-2-(methoxyphenyl)-8-(1-methylpropyl)-5,6,7,8-tetrahydroimidazo[1,2a]pyrazine]disulfide (Compound 20);

bis-1,1'-[7-(2-amino-1-oxo-3-thiopropyl)-8-butyl-2-(2-methylphenyl)-5,6,7,8-tetrahydroimidazo[1,2a]pyrazine]disulfide (Compound 23).

bis-1,1'-[7-(2-amino-1-oxo-3-thiopropyl)-2-(2-methoxyphenyl)-8-(1-methylethyl)-5,6,7,8-tetrahydroimidazo[1,2a]]pyrazine]disulfide (Compound 28).

bis-1,1'-[7-(2-amino-1-oxo-3-thiopropyl)-8-(1,1-dimethylethyl)-2-(2-methoxyphenyl)-5,6,7,8-tetrahydroimidazo[1,2a]pyrazine]disulfide (Compound 30);

bis-1,1'-[2-amino-3-(8-butyl-2-cyclohexyl-5,6,7,8-tetrahydro-imidazo-[1,2a]pyrazin-7-yl)-3-oxo-propyl] disulfide (Compound 33);

bis-1,1'-[2-amino-3-(3-bromo-8-butyl-2-phenyl-5,6,7,8-tetrahydro-imidazo[1,2a]-pyrazin-7-yl)-3-oxo-propyl] disulfide (Compound 35);

bis-1,1'-[7-(2-amino-1-oxo-3-thiopropyl)-8-butyl-2,3-diphenyl-5,6,7,8-tetrahydroimidazo[1,2a]pyrazine] disulfide (Compound 38);

bis-1,1'-[7-(2-amino-1-oxo-3-thiopropyl)-8-(1-methylpropyl)-2-(2-(phenylmethoxy)phenyl)-5,6,7,8-tetrahydroimidazo[1,2a]pyrazine]disulfide (Compound 39);

bis-1,1'-[2-amino-3-(2-cyclohexyl-8-(cyclohexylmethyl)-5,6,7,8-tetrahydro-imidazo[1,2a]pyrazin-7-yl)-3-oxo-propyl]disulfide (Compound 40);

bis-1,1'-[7-(2-amino-1-oxo-3-thiopropyl)-8-(cyclohexylmethyl)-2-(2-methoxyphenyl)-5,6,7,8-tetrahydroimidazo[1,2a]pyrazine]disulfide (Compound 41);

bis-1,1'-[7-(2-amino-1-oxo-3-thiopropyl)-8-hexyl-2-(2-methoxyphenyl)-5,6,7,8-tetrahydro-imidazo[1,2a]pyrazine]disulfide (Compound 43);

bis-1,1'-[7-(2-amino-1-oxo-3-thiopropyl)-8-(cyclohexylethyl)-2-(2-methoxyphenyl)-5,6,7,8-tetrahydroimidazo[1,2a]pyrazine]disulfide (Compound 45);

bis-1,1'-[7-(2-amino-1-oxo-3-thiopropyl)-8-(cyclohexyl)-2-(2-methoxyphenyl)-5,6,7,8-tetrahydroimidazo[1,2a]pyrazine ]disulfide (Compound 48); and bis-1,1'-[7-(2-amino-1-oxo-3-thiopropyl)-8-(2-(4-methoxycyclohexyl)-methyl)-2-(2-methoxyphenyl)-5,6,7,8-tetrahydroimidazo[1,2a]pyrazine]disulfide (Compound 50);

The structures of these compounds are listed in Table I below.

TABLE I

COMPOUND 1

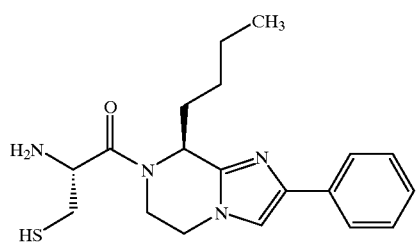

COMPOUND 2

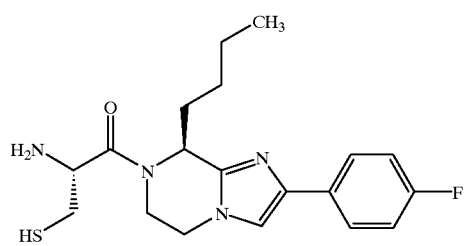

TABLE I-continued
COMPOUND 3
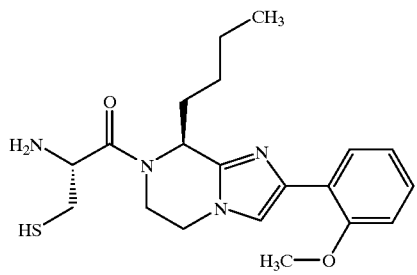
COMPOUND 4
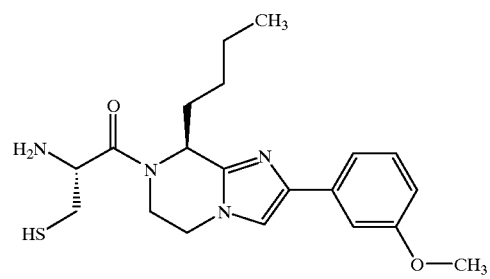
COMPOUND 5
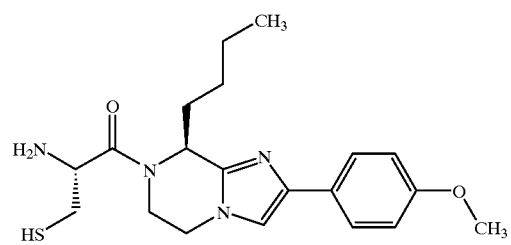
COMPOUND 6
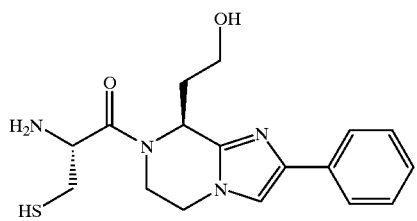
COMPOUND 7
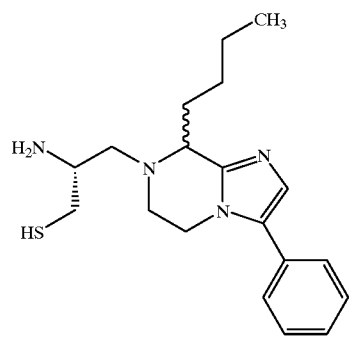

TABLE I-continued
COMPOUND 8
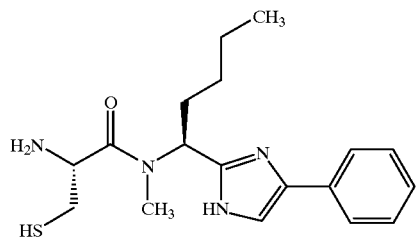
COMPOUND 9
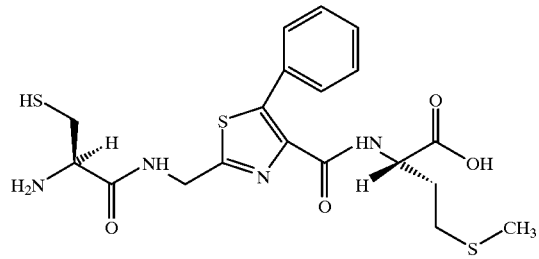
COMPOUND 10
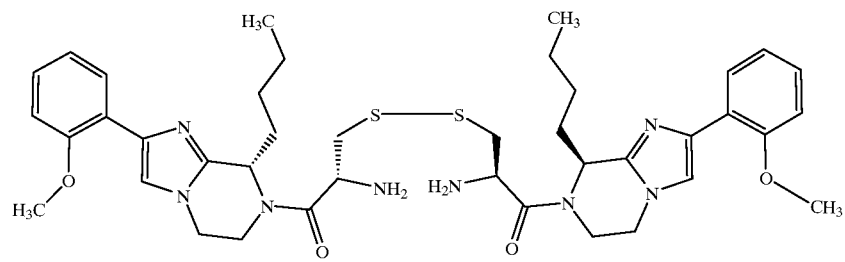
COMPOUND 11
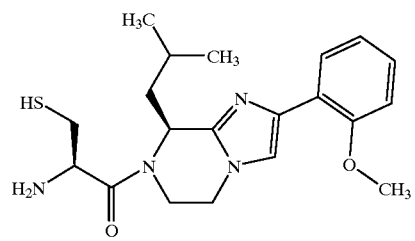
COMPOUND 12
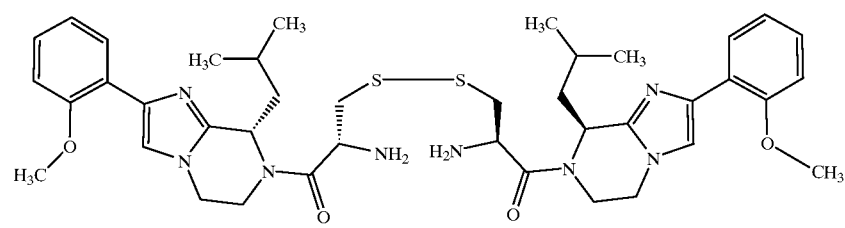
COMPOUND 13
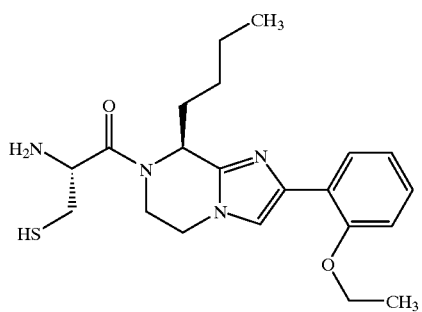

TABLE I-continued
COMPOUND 14
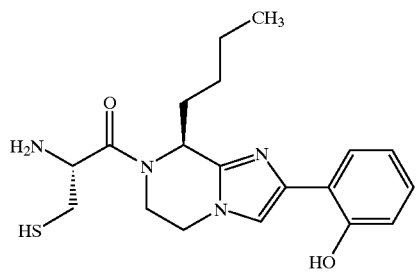
COMPOUND 15
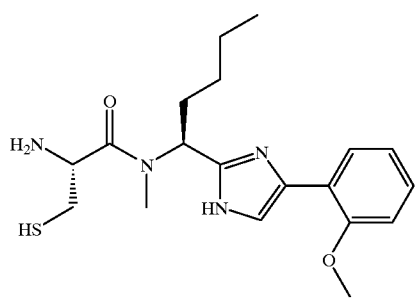
COMPOUND 16
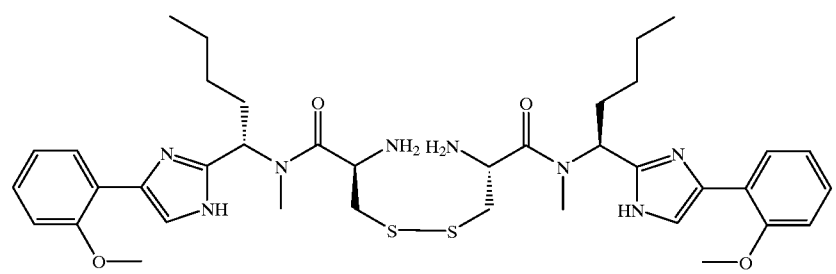
COMPOUND 17
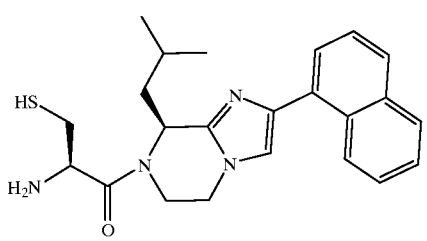
COMPOUND 18
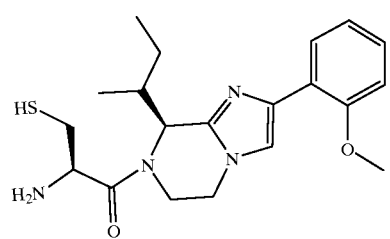
COMPOUND 19
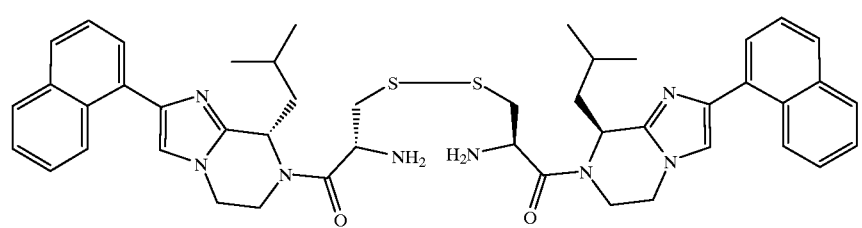

TABLE I-continued
COMPOUND 20
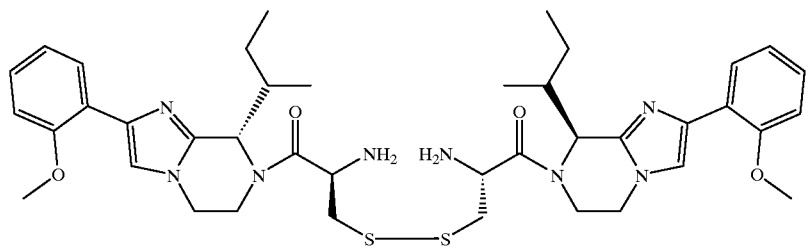
COMPOUND 21
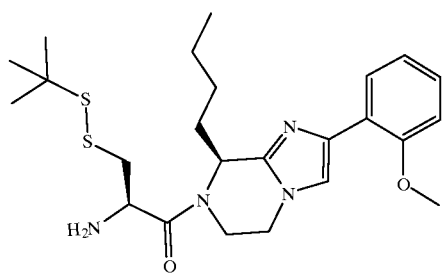
COMPOUND 22
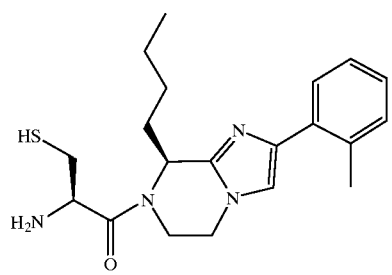
COMPOUND 23
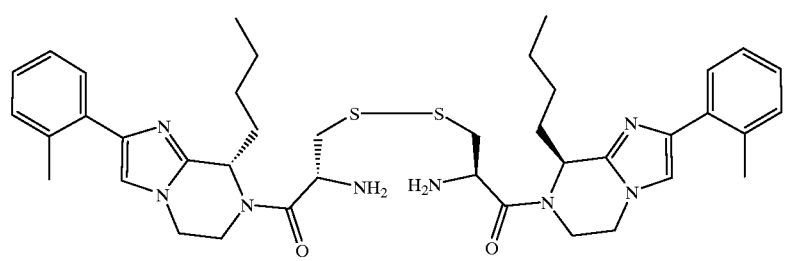
COMPOUND 24
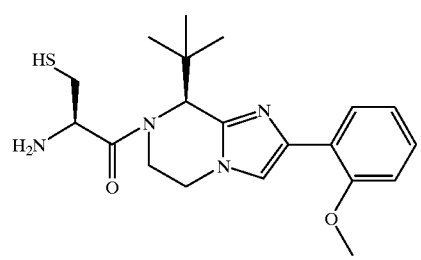

TABLE I-continued
COMPOUND 25
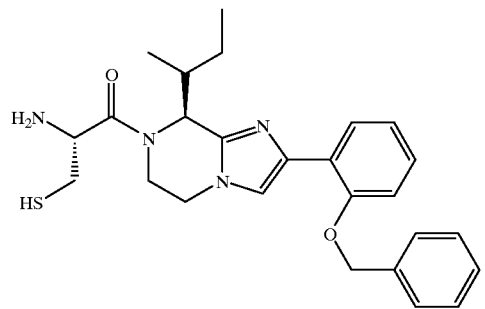
COMPOUND 26
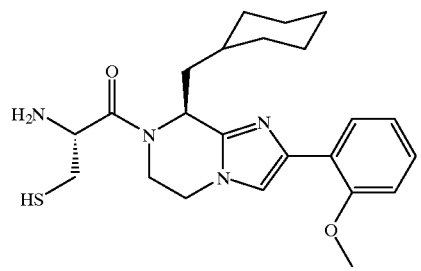
COMPOUND 27
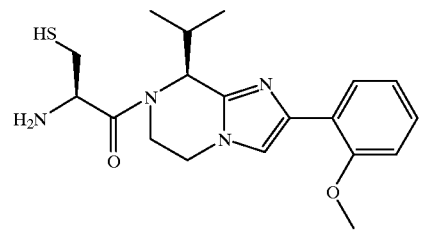
COMPOUND 28
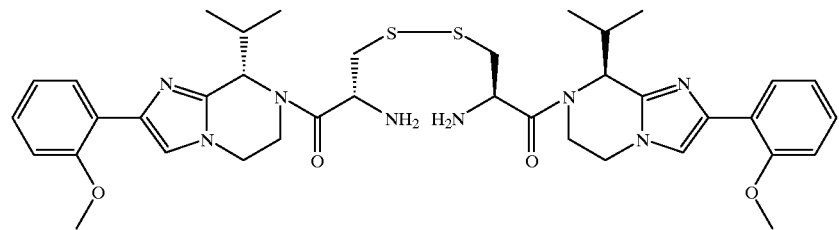
COMPOUND 29
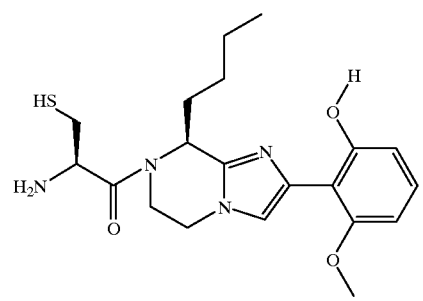

TABLE I-continued
COMPOUND 30
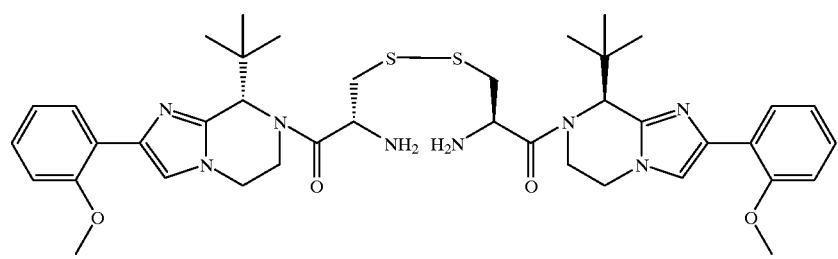
COMPOUND 31
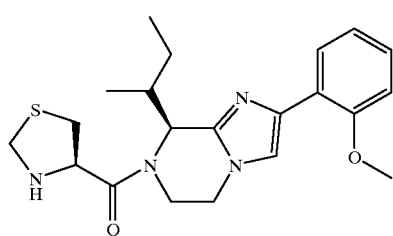
COMPOUND 32
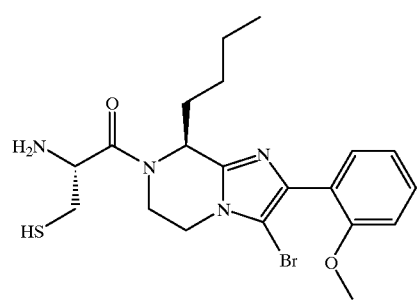
COMPOUND 33
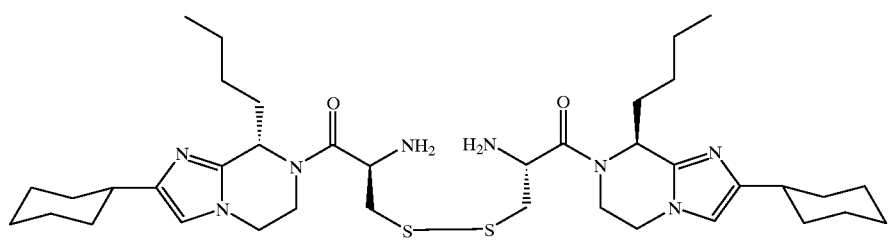
COMPOUND 34
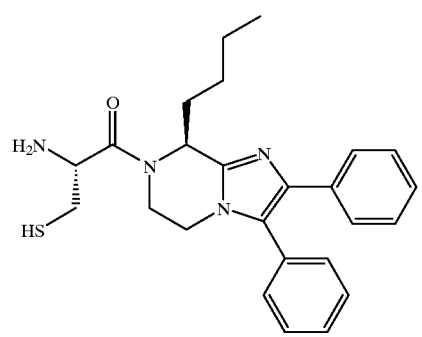

TABLE I-continued
COMPOUND 35
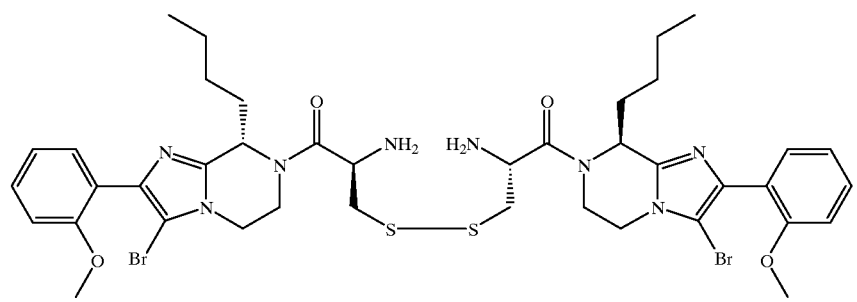
COMPOUND 36
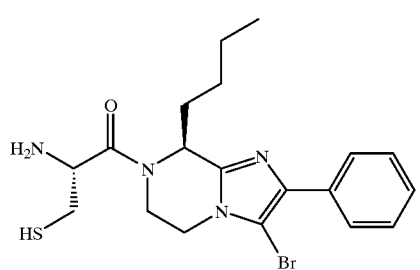
COMPOUND 37
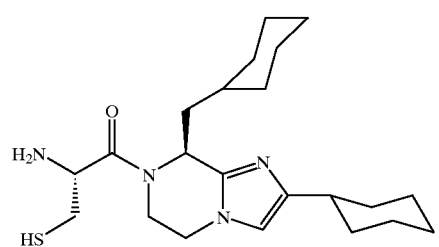
COMPOUND 38
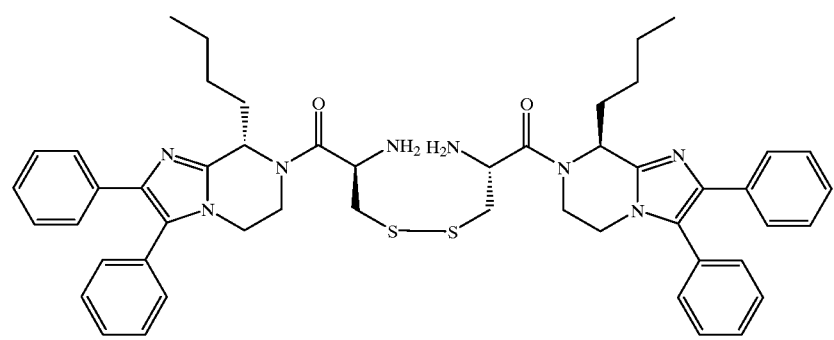
COMPOUND 39
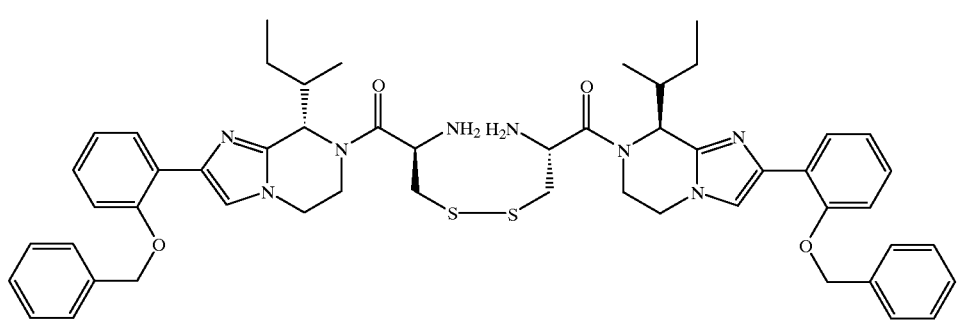

TABLE I-continued
COMPOUND 40
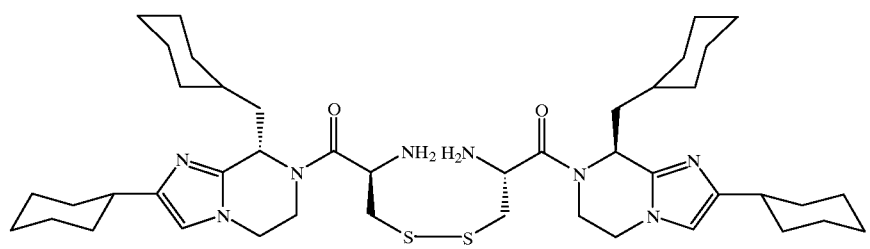
COMPOUND 41
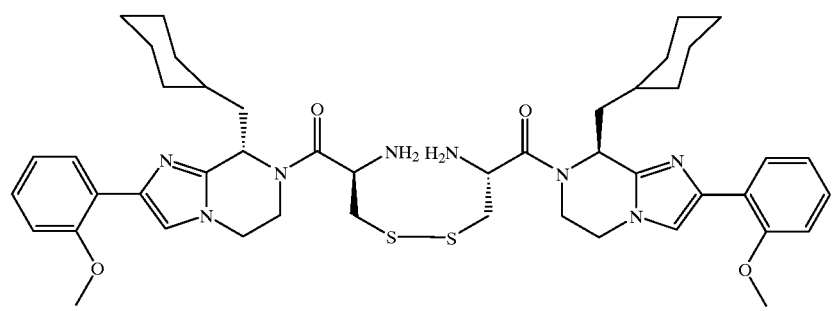
COMPOUND 42
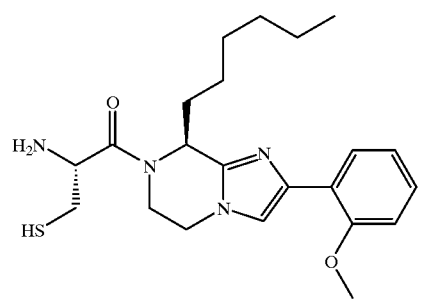
COMPOUND 43
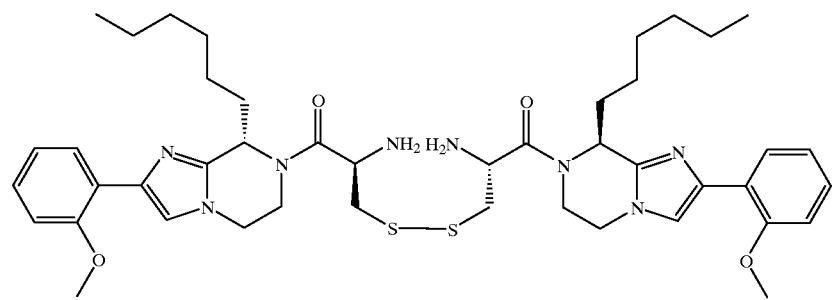
COMPOUND 44
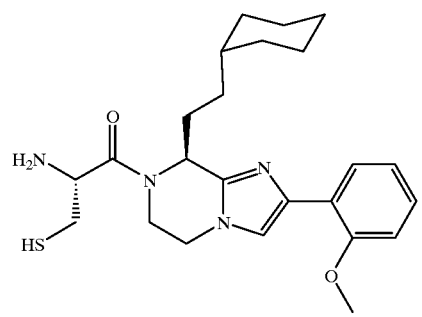

TABLE I-continued
COMPOUND 45
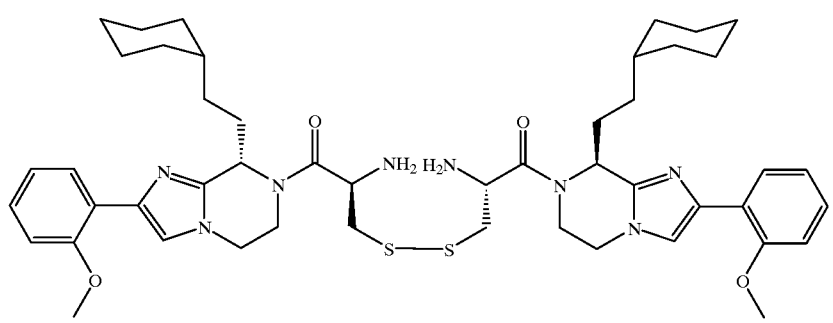
COMPOUND 46
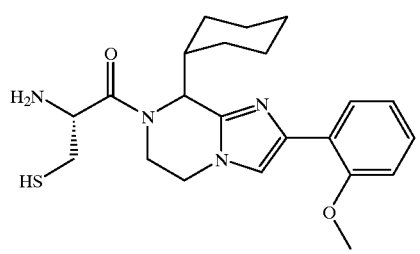
COMPOUND 47
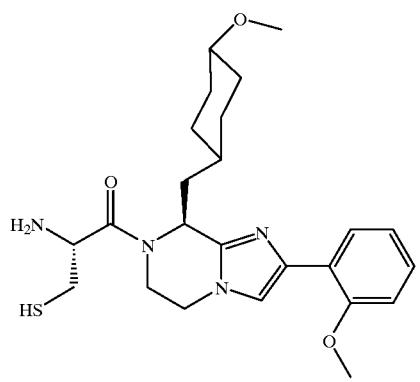
COMPOUND 48
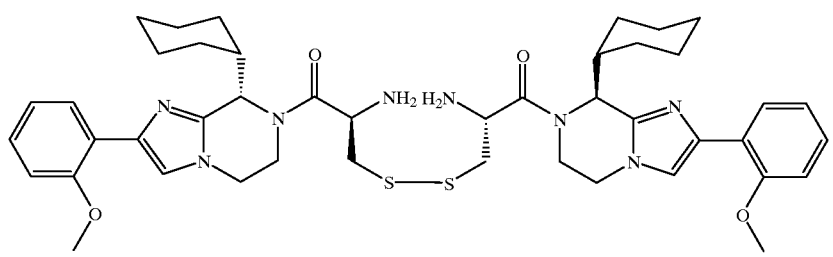
COMPOUND 49
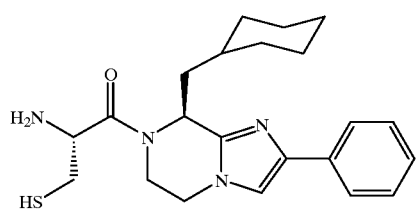

TABLE I-continued
COMPOUND 50
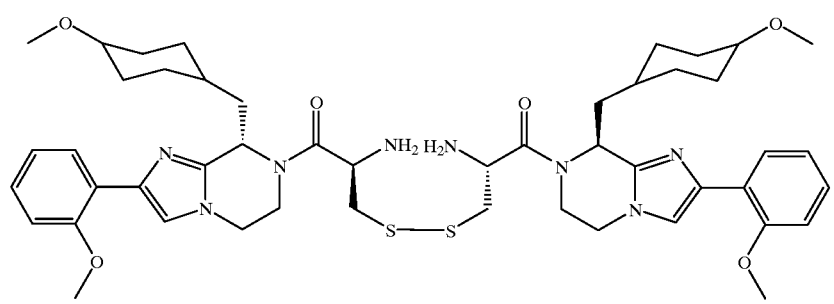
COMPOUND 51
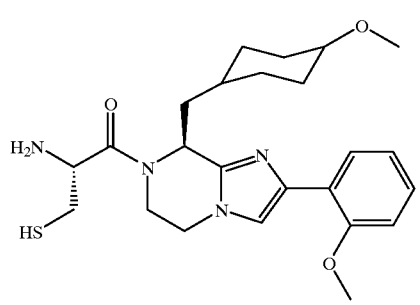
COMPOUND 52
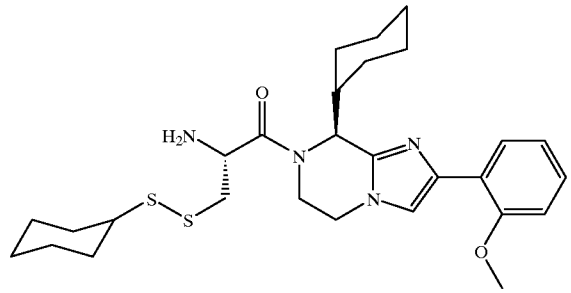
COMPOUND 53
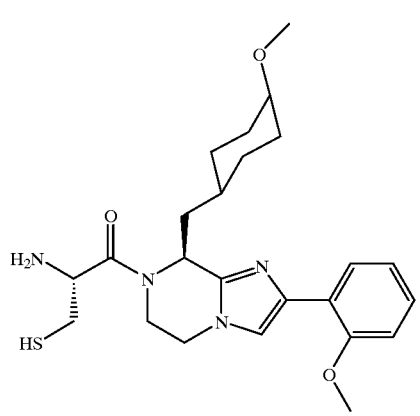
COMPOUND 54
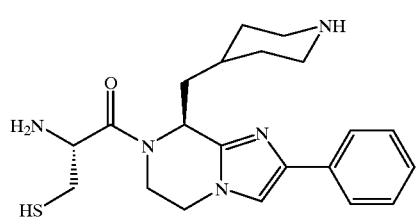

TABLE I-continued
COMPOUND 55
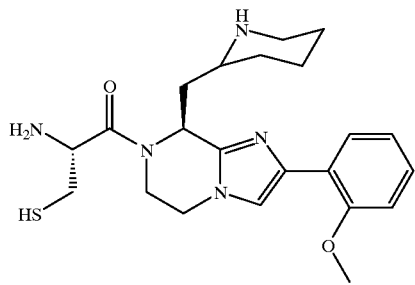
COMPOUND 56
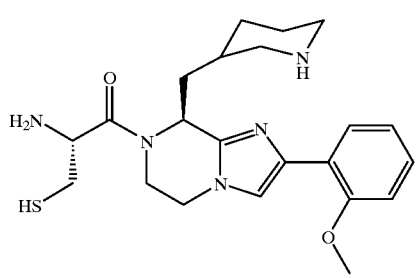
COMPOUND 57
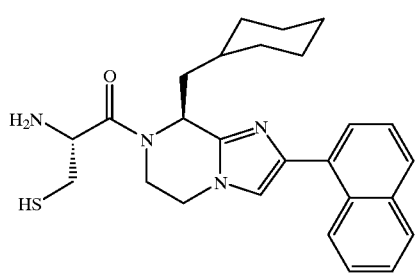
COMPOUND 58
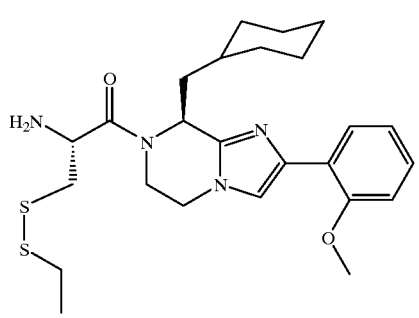
COMPOUND 59
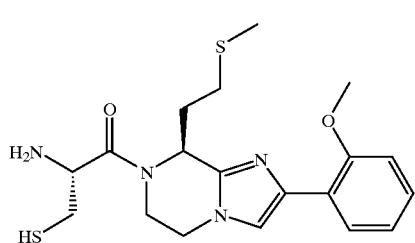

TABLE I-continued

COMPOUND 60

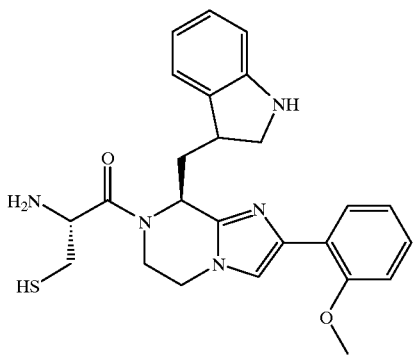

COMPOUND 61

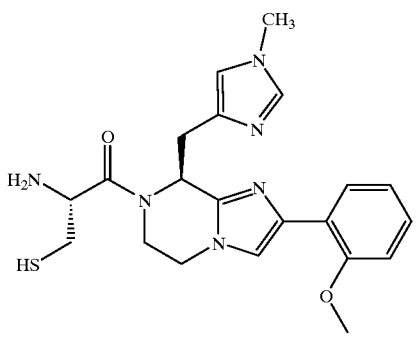

The compounds of the present invention may have asymmetric centers and occur as racemates, racemic mixtures, and as individual diastereomers, with all possible isomers, including optical isomers, being included in the present invention. For simplicity, where no specific configuration is depicted in the structural formulae, it is understood that all enantiometric forms and mixtures thereof are represented.

As used herein, "lower alkyl" is intended to include both branched and straight-chain saturated aliphatic hydrocarbon groups having 1–6 carbon atoms. Examples of lower alkyl groups include methyl, ethyl, propyl, isopropyl, butyl, t-butyl, isobutyl, sec-butyl, and the like. "Lower alkenyl" groups include those groups having 2–6 carbon atoms and having one or several double bonds. Examples of alkenyl groups include vinyl, allyl, isopropenyl, butenyl, pentenyl, hexenyl, 1-propenyl, 2-butenyl, 2-methyl-2-butenyl, isoprenyl, and the like. "Alkynyl groups" include those groups having 2–6 carbon atoms and having one or several triple bonds. Examples of alkynyl groups include ethynyl, propynyl, 1-butynyl, 2-butynyl, 3-butynyl, s-butynyl, and the like. All alkyl, alkenyl, and alkynyl groups are noncyclic.

As used herein, "cycloalkyl" is intended to include non-aromatic cyclic hydrocarbon groups having 3–10 carbon atoms. Examples of cycloalkyl groups include cyclopropyl, cyclobutyl, cyclopentyl, cyclobenzyl, and the like. "Cycloalkenyl" is intended to include non-aromatic hydrocarbon cyclic groups having 3–10 carbon atoms and having one or several double bonds. Examples of cycloalkenyl groups include cyclopropenyl, cyclobutenyl, cyclopentenyl, and cyclohexyl, and the like.

As used herein, "aryl" is intended to include any stable monocyclic, bicyclic, or tricyclic carbon ring(s) of up to 7 members in each ring, wherein at least one ring is aromatic. Examples of aryl groups include phenyl, naphthyl, anthracenyl, biphenyl, tetrahydronaphthyl, indanyl, phenanthrenyl, and the like.

The term heterocyclyl, as used herein, represents a stable 5- to 7-membered monocyclic or stable 8- to 11-membered bicyclic or stable 11–15 membered tricyclic heterocyclic ring which is either saturated or unsaturated, and which consists of carbon atoms and from one to four heteroatoms selected from the group consisting of N, O, and S, and including any bicyclic group in which any of the above-defined heterocyclic rings is fused to a benzene ring. The heterocyclic ring may be attached at any heteroatom or carbon atom which results in the creation of a stable structure. Examples of such heterocyclic elements include, but are not limited to, azepinyl, benzimidazolyl, benzisoxazolyl, benzofurazanyl, benzopyranyl, benzothiopyranyl, benzofuryl, benzothiazolyl, benzothienyl, benzoxazolyl, chromanyl, cinnolinyl, dihydrobenzofuryl, dihydrobenzothienyl, dihydrobenzothiopyranyl, dihydrobenzothio-pyranyl sulfone, furyl, imidazolidinyl, imidazolinyl, imidazolyl, indolinyl, indolyl, isochromanyl, isoindolinyl, isoquinolinyl, isothiazolidinyl, isothiazolyl, isothiazolidinyl, morpholinyl, naphthyridinyl, oxadiazolyl, 2-oxoazepinyl, 2-oxopiperazinyl, 2-oxopiperidinyl, 2-oxopyrrolidinyl, piperidyl, piperazinyl, pyridyl, pyridyl N-oxide, quinoxalinyl, tetrahydrofuryl, tetrahydroisoquinolinyl, tetrahydro-quinolinyl, thiamorpholinyl, thiamorpholinyl sulfoxide, thiazolyl, thiazolinyl, thienofuryl, thienothienyl, thienyl, and the like.

The term halo is meant to include fluoro, chloro, bromo, and iodo.

The term "substituted" is meant to include the recited chemical group (e.g., lower alkyl, heterocycle, aryl, cycloalkyl, etc.) substituted with one to four of the recited substituents (e.g., halo, OH, lower alkyl, etc.). The substituent may be attached to any atom in the chemical group.

The compounds of this invention can be provided in the form of pharmaceutically acceptable salts. Acceptable salts include, but are not limited to, acid addition salts of inorganic acids such as hydrochloride, sulfate, phosphate, diphosphate, hydrobromide, and nitrate or organic acids such as acetate, maleate, fumarate, tartrate, succinate, citrate, lactate, methanesulfonate, p-toluenesulfonate, pamoate, salicylate, oxalate, and stearate. Also within the scope of the present invention, where applicable, are salts formed from bases such as sodium or potassium hydroxide. For further examples of pharmaceutically acceptable salts see, "Pharmaceutical Salts," J. Pharm. Sci. 66:1 (1977).

In another aspect, the invention features a method of inhibiting farnesyl transferase in a patient, e.g., a mammal such as a human, by administering to a patient a therapeutically effective amount of a compound of formula (I) or formula (II). In particular, the present invention also covers a method of treating restenosis or tissue proliferative diseases (i.e., tumor) in a patient by administering to a patient a therapeutically effective amount of a compound or its salt. Examples of tissue proliferative disease include both those associated with benign (e.g., non-malignant) cell proliferation such as fibrosis, benign prostatic hyperplasia, atherosclerosis, and restenosis, and those associated with malignant cell proliferation, such as cancer (e.g., tumors expressing farnesyl transferase). Examples of treatable tumors are breast, colon, pancreas, prostate, lung, ovarian, epidermal, and hematopoietic cancers (Sepp-Lorenzino, I, et al., Cancer Research 55:5302 (1995)).

A therapeutically effective amount of a compound of this invention and a pharmaceutically acceptable carrier substance (e.g., magnesium carbonate, lactose, or a phospholipid with which the therapeutic compound can form a micelle) together form a therapeutic composition (e.g., a pill, tablet, capsule, or liquid) for administration (e.g., orally, intravenously, transdermally, or subcutaneously) to a subject in need of the compound. The pill, tablet, or capsule can be coated with a substance capable of protecting the composition from the gastric acid or intestinal enzymes in the subject's stomach for a period of time sufficient to allow the composition to pass undigested into the subject's small intestine.

The dose of a compound of the present invention for treating the above-mentioned diseases or disorders varies depending upon the manner of administration, the age and the body weight of the subject, and the condition of the subject to be treated, and ultimately will be decided by the attending physician or veterinarian. Such an amount of the compound as determined by the attending physician or veterinarian is referred to herein as a "therapeutically effective amount."

Also contemplated within the scope of the invention is a method of preparing the compound of formula (I) or formula (II) and the novel chemical intermediates used in these syntheses as described herein.

Other features and advantages of the present invention will be apparent from the detailed description of the invention and from the claims.

DESCRIPTION OF THE INVENTION

It is believed that one skilled in the art can, based on the description herein, utilize the present invention to its fullest extent. The following specific embodiments are to be construed as merely illustrative, and not limitative of the remainder of the disclosure in any way whatsoever.

Unless defined otherwise, all technical and scientific terms used herein have the same meaning as commonly understood by one of ordinary skill in the art to which this invention belongs. Also, all publications, patent applications, patents, and other references mentioned herein are incorporated by reference.

Synthesis

The following is a description of the synthesis of compounds 1 to 31. Other compounds of the invention can be prepared in an analogous manner by a person of ordinary skill in the art. As used herein, the term Cbz means carbobenzyloxy; DMF means dimethylformamide; EtOAc means ethyl acetate, $NH_4OAc$ means ammonium acetate; LAH means lithium aluminum hydride; THF means tetrahydrofuran; BOC means t-Butoxycarbonyl; Trt means trityl; Tfa means trifluoroacetic acid; $Et_2O$ means ethyl ether; NMR means nuclear magnetic resonance; mass spec. means mass spectroscopy; DMSO-d6 means methyl sulfoxide; DCC means dicyclohexyl carbodiimide; NMM means 4-methyl morpholine; $iPr_3SiH$ means triisopropylsilane, HPLC means high performance liquid chromatography; DIC means diisopropylcarbodiimide; MeOH means methanol; KOtBu means potassium tert-butoxide; HOSU means N-hydroxysuccinimide; and iBuOCOCl means isobutyl chloroformate.

EXAMPLE 1

7-(2-Amino-1-oxo-3-thio-propyl)-8-butyl-2-phenyl-5,6,7,8-tetrahydro-imidazo-[1,2a]-pyrazine
(Compound 1)

Compound 1 was synthesized according to synthetic scheme 1 as shown below:

SCHEME 1

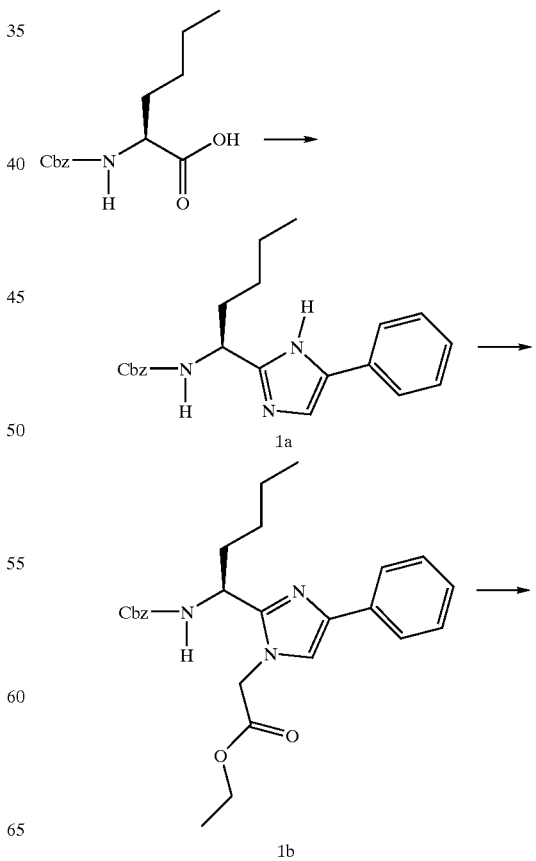

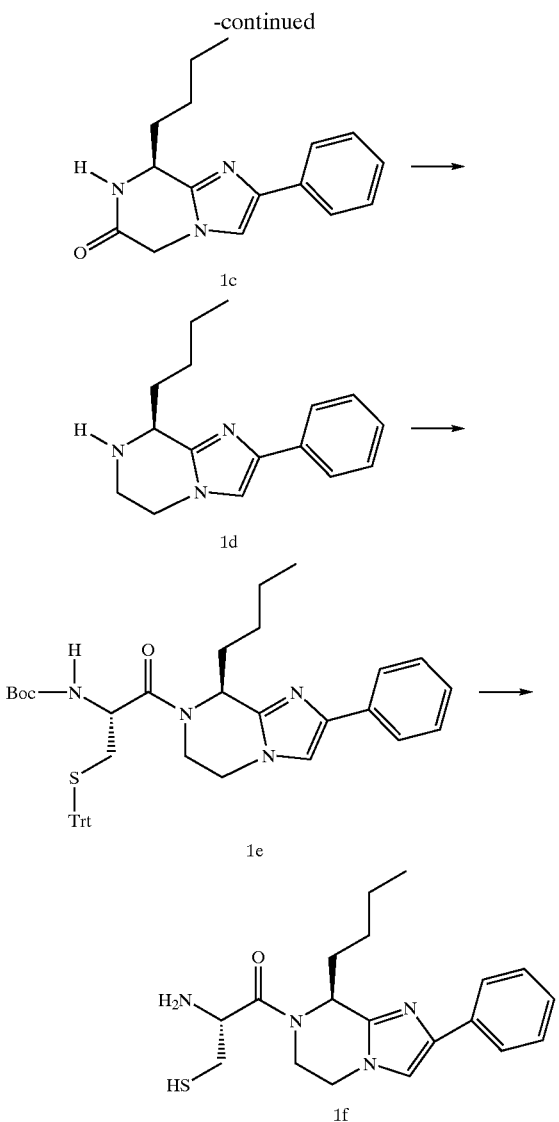

a. 2-[1-(S)-(((Phenylmethoxy)carbonyl)amino)-pentyl]-4-phenyl-imidazole

Cbz-(L)-Norleucine (10.0 g, 37.7 mmole) and Cs$_2$CO$_3$ (6.14 g, 18.9 mmole) were combined in 1:1/DMF:H$_2$O (75 ml), and the mixture was swirled until a homogeneous mixture was obtained. Solvents were removed in vacuo. The residue was dissolved in DMF (50 ml), and the solvents were removed in vacuo again to remove any residual H$_2$O. The residue was dissolved in DMF (50 ml), and 2-bromoacetophenone (7.5 g, 37.7 mmole) in DMF (25 ml) was added to the solution. The solution was stirred for 15 min. at room temperature and then concentrated in vacuo. The resulting keto-ester was dissolved in EtOAc (75 ml), CsBr was filtered off, and the solution was concentrated in vacuo. NH$_4$OAc (50.0 g, 0.65 mole) and xylenes (150 ml) were added to the solution, and the solution was heated at reflux for 1.5 hr. The solution was then cooled, and the solvents were removed in vacuo. The residue was dissolved in EtOAc (75 ml) and washed two times with saturated NaHCO$_3$ solution (50 ml). The EtOAc layer was then dried over MgSO$_4$, filtered, and hexanes were added to turbidity. The resulting crystalline product was filtered off, and the product was dried to yield 10.04 g (73%) of product. m.r.=136–138C, Mass spec. (MH$^+$364.3). NMR (300 MHz, CD$_3$CO$_2$D) 7.7 (3H, m), 7.4 (3H, m), 7.3 (5H, m), 5.1 (3H, m), 2.1 (2H, m (obscured by solvent)), 1.4 (4H, M), 0.9 (3H, t).

b. Ethyl, 2-[1-(S)-(((Phenylmethoxy)carbonyl)amino)-pentyl]-4-phenyl-1-imidazoleacetate Ethyl bromoacetate (2.64 ml, 24 mmole), K$_2$CO$_3$ (1.93 g, 14.0 mmole), and intermediate 1a (4.36 g, 12.0 mmole) were mixed in DMF (25 ml), and the mixture was heated at 60° C. for 4 hr. The mixture was then concentrated in vacuo and the residue was dissolved in EtOAc (50 ml). The solution was washed with both a saturated NaHCO$_3$ solution (25 ml) and a saturated NaCl solution (25 ml). The solution was then dried over MgSO$_4$, filtered, and the solvents were removed in vacuo. The residue was further purified by flash chromatography on silica gel using 80:20/hexanes:EtOAc as an eluant. Pure product fractions were combined and concentrated in vacuo to yield an oil which was crystallized. as 3.09 g (57%) of product. m.r.=85–87° C., mass spec. 450.2 (MH+), 472.2 (MNa+). NMR (300 MHz, CD$_3$CO$_2$D) 7.7 (2H, d), 7.5 (1H, s), 7.2–7.45 (8H, m), 5.25 (2H, dd), 5.1 (2H, dd), 5.1 (1H, m), 2.15 (2H, m), 1.4 (7H, m), 0.9 (3H, t).

c. (S)-8-Butyl-6-oxo-2-phenyl-5,6,7,8-tetrahydro-imidazo-[1,2a]-pyrazine

Intermediate 1c (2.89 g, 6.44 mmole) was dissolved in 50 ml acetic acid containing 290 mg of 10% Pd on carbon. The mixture was hydrogenated for 8 hrs at room temperature. The catalyst was removed by filtration through celite. Lactamization was accomplished by heating at 70° C. for 3 hrs. The product was concentrated under reduced pressure, and the residue was distributed between EtOAc and a saturated NaHCO$_3$ solution. The EtOAc layer was dried over MgSO$_4$ and filtered. The product was crystallized from EtOAc/hexanes to yield 1.37 g (79%) of product. m.r.=208–211C, mass spec. 270.2 (MH+), 292.2 (MNa+). NMR (300 MHz, CD$_3$CO$_2$D) 7.75 (2H, d), 7.5 (1H, s), 7.3–7.45 (3H, m), 5.25 (1H, m), 4.95 (2H, s), 2.1 (2H, m (obscured by solvent peak)), 1.4 (4H, m), 0.9 (3H, t).

d. (S)-8-Butyl-2-phenyl-5,6,7,8-tetrahydro-imidazo-[1,2a]-pyrazine

A solution of intermediate 1c (1.25 g, 4.65 mmole) in 20 ml THF was added dropwise to a stirred solution of 1M LAH in THF (16 ml). The mixture was heated to reflux for 1 hr. and then stirred at room temperature overnight. The mixture was then quenched by the slow addition of a mixture of 3 g celite and 2 ml of a saturatd K$_2$CO$_3$ solution. The mixture was stirred for 1 hr., and filtered solids were extracted three times with 25 ml EtOAc. Solvents were removed under reduced pressure, and the residue was purified by flash chromatography on silica gel using ethyl acetate:acetic acid:pyridine:water/900:54:16:30 as an eluant. The product fractions were concentrated to oil and then taken up in ethyl acetate. The solution was washed with 25 ml of saturated NaHCO$_3$, dried over MgSO$_4$, filtered, and concentrated in vacuo. The product was dried on a vacuum pump to yield 190 mg (16%) of product. Mass spec. 256.2 (MH+), 278.2 (MNa+).

e. 7-[2-(((1,1-Dimethylethoxy)carbonyl)amino)-1-oxo-3-((triphenylmethyl)thio)propyl]-8-Butyl-2-phenyl-5,6,7,8-tetrahydro-imidazo-[1,2a]-pyrazine Dicyclohexylcarbodiimide (155 mg, 0.75 mmole) and Boc-Cys(Trt)-OH (Advanced Chemtech) were dissolved in 8 ml of THF and stirred for 5 min. The resulting dicyclohexylurea was filtered off, and the filtrate was added to intermediate 1d. The resulting mixture was stirred at room temperature for 6 hrs, concentrated to a gum, and purified by flash chromatography on silica gel using 7:3/hexanes:EtOAc as an eluant. Product fractions were combined and concentrated to a glass yielding 500 mg (95%) of product. Mass spec. 701.5 (MH+), 723.5 (MNa+). NMR (300 MHz, CD$_3$CO$_2$D), 7.7 (2H, d), 7.5 (1H, s), 7.2–7.45 (18H, m), 6.05 (1H, d), 4.6 (1H, t) 4.2 (2H, t), 3.95 (1H, t), 3.8 (1H, m), 2.6 (2H, m), 2.0 (2H,m (obscured by solvent)), 1.4 (9H, s), 1.2–1.4 (4H, m), 0.9 (3H, t)

f. 7-(2-Amino-1-oxo-3-thio-propyl)-8-butyl-2-phenyl-5,6,7,8-tetrahydro-imidazo-[1,2a]-pyrazine (Compound 1)

Intermediate 1e (322 mg, 0.46 mmole) was stirred with 10 ml of Reagent B (Tfa:phenol:(iPr₃SiH):H₂O/8.8:0.5:0.2:0.5) under nitrogen for 15 min. The solvents were removed under reduced pressure, and the residue was taken up in 25 ml H₂O and washed two times with 25 ml Et₂O. The aqueous layer was purified by reverse phase column chromatography to provide 9 mg (5%) of compound 1 as a white lyophilized powder. Mass spec: 359.1 (MH+).

EXAMPLE 2

7-(2-Amino-1-oxo-3-thio-propyl)-8-butyl-2-(4-fluorophenyl)-5,6,7,8-tetrahydro-imidazo-[1,2a]-pyrazine (Compound 2)

Compound 2 was prepared by in a manner analogous to Example 1 except that 2-bromo-4'-fluoro-acetophenone was used in place of 2-bromoacetophenone in step a. Mass spec. 377.2 MH+. NMR (300 MHz, CD₃CO₂D), (approximately 2 to 1 mixture of conformers observed) 7.8–8.0 (2H, m), 7.6–7.8 (1H, s), 7.1–7.3 (12H, m), 5.8–6.3(1H, m), 3.5–5.3 (5H, t), 3.0–3.4 (2H, m), 2.1–2.6 (2H, m), 1.3–1.7 (4H, m), 0.8–1.0 (3H, m).

EXAMPLE 3

7-(2-Amino-1-oxo-3-thio-propyl)-8-butyl-2-(2-methoxy-phenyl)-5,6,7,8-tetrahydro-imidazo-[1,2a])-pyrazine (Compound 3)

Compound 3 was prepared in a manner analogous to Example 1 except that 2-bromo-2'-methoxy-acetophenone was used in place of 2-bromoacetophenone in step a. Mass spec. 389.3 MH+. NMR (300 MHz, DMSO-d6), 8.2–8.8 (3H, s), 7.7–8.0 (2H, m), 7.2–7.4 (1H, m), 6.8–7.2(2H, m), 5.4–5.8 (1H,t), 4.5–4.8 (1H, t), 3.7–4.5 (4H, m), 3.9(3H, s), 2.7–3.1 (2H, m), 1.8–2.1 (2H, m) 1.3–1.6 (4H, m), 0.8–1.0 (3H, t).

EXAMPLE 4

7-(2-Amino-1-oxo-3-thio-propyl)-8-butyl-2-(3-methoxy-phenyl)-5,6,7,8-tetrahydro-imidazo-[1,2a]-pyrazine (Compound 4)

Compound 4 was prepared in a manner analogous to Example 1 except that 2-bromo-3'-methoxy-acetophenone was used in place of 2-bromoacetophenone in step a. Mass spec. 389.3 MH+. NMR (300 MHz, DMSO-d6), ), (approximately 4 to 1 mixture of conformers observed) 8.2–8.7 (3H, s), 7.7–8.0 (1H, s), 7.2–7.5 (3H, m), 6.8–7.0 (2H, d), 5.4–5.8 (1H, t), 4.5–4.8 (1H, t), 3.7–4.5 (4H, m), 3.8 (3H, s), 2.7–3.1 (2H, m), 1.8–2.1 (2H, m) 1.2–1.6 (4H, m), 0.8–1.0 (3H, t).

EXAMPLE 5

7-(2-Amino-1-oxo-3-thio-propyl)-8-butyl-2-(4-methoxy-phenyl)-5,6,7,8-tetrahydro-imidazo-[1,2a]-pyrazine (Compound 5)

Compound 5 was prepared in a manner analogous to Example 1 except that 2-bromo-4'-methoxy-acetophenone was used in place of 2-bromoacetophenone in step a. Mass spec. 389.2 MH+. NMR (300 MHz, DMSO-d6), ), (approximately 6 to 1 mixture of conformers observed) 8.2–8.8 (3H, s), 7.7–8.0 (1H, s), 7.5–7.8 (2H, d), 6.9–7.2 (2H, d), 5.4–5.8 (1H, t), 4.5–4.8 (1H, t), 3.7–4.5 (4H, m), 3.8 (3H, s), 2.7–3.2 (2H, m), 1.8–2.1 (2H, m) 1.2–1.6 (4H, m), 0.8–1.0 (3H, t).

EXAMPLE 6

7-(2-Amino-1-oxo-3-thio-propyl)-8-(2-hydroxy-ethyl)-2-phenyl-5,6,7,8-tetrahydro-imidazo-[1,2a]-pyrazine (Compound 6)

Compound 6 was prepared in a manner analogous to Example 1 except that 2-bromo-4'-methoxy-acetophenone in place of 2-bromoacetophenone in step a. Mass spec. 347.1 MH+.

EXAMPLE 7

7-(2-Amino-3-thio-propyl)-8-butyl-3-phenyl-5,6,7,8-tetrahydro-imidazo-[1,2a]-pyrazine (Compound 7)

Compound 7 was synthesized according to synthetic Scheme 2 as set forth below:

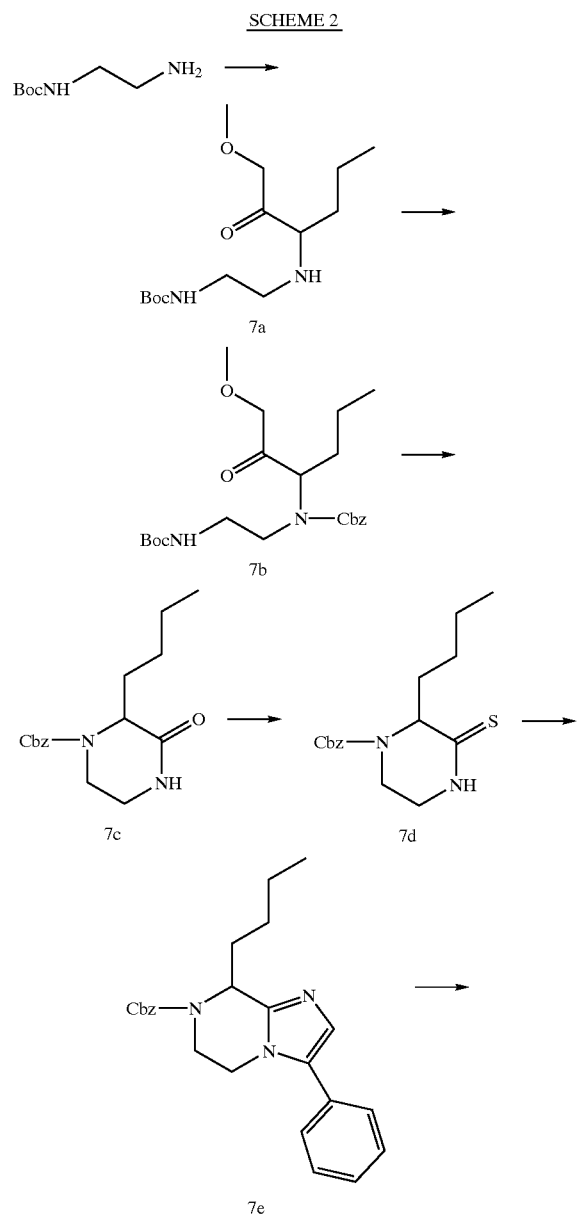

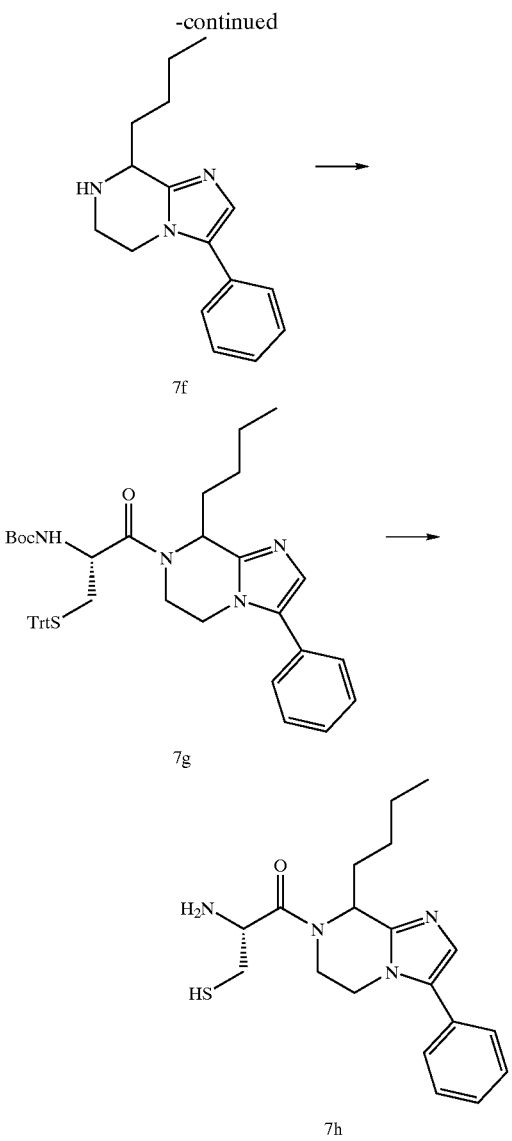

7f

7g

7h a. Ethyl, 2-((2-(((1,1-Dimethylethoxy-)carbonyl-)amino-)ethyl-)amino-)-hexanoate Boc-NHCH$_2$CH$_2$NH$_2$ was prepared as described by A. P. Krapcho and C. S. Kuell, Syn. Comm. 20(16):2559–2564 (1990). Boc-NHCH$_2$CH$_2$NH$_2$ (5.00 g, 31.25 mmole), ethyl 2-bromohexanoate (5.71 ml, 31.25 mmole), and K$_2$CO$_3$ (4.31 g, 31.25 mmole) were combined in 75ml DMF and stirred at 40° C. for 1.5 hr. Solvents were removed under reduced pressure, and the residue was then distributed between Et$_2$O and H$_2$O. The ether layer was dried over MgSO$_4$ and filtered, and the solvents were removed under reduced pressure to yield 7.48 g (79%) of an oil. Mass spec. 303.0 MH+, NMR (CDCl$_3$), 4.9–5.1 (1H, S br), 4.1–4.4 (2H, M), 3.0–3.6 (2H, M), 2.5–3.0 (2H, M), 1.9–2.2 (1H, S br), 1.3–1.8 (2H, M), 1.5 (9H, S), 1.2–1.5 (7H, M), 0.8–1.0 (3H t).

b. Ethyl, 2-(N-(2-(((1,1-Dimethylethoxy-)carbonyl-)amino-)ethyl-)]-N-[(phenylmethoxy)carbonyl-]aminohexanoate Intermediate 7a (7.40 g, 24.5 mmole) was dissolved in 40 ml THF, and 10 ml H$_2$O was then added. The mixture was cooled to 5° C., and Cbz-Cl was added in four portions to the mixture. The pH of the mixture was maintained between 8–9 by addition of 2.5N NaOH. When the reaction was completed, the solvents were removed under vacuum, and the residue was taken up in EtOAc and washed with 5% citric acid solution. The solvents were removed under reduced pressure. The residue was dissolved in hexanes, filtered to remove a crystalline impurity, and dried to yield 7.34 g (69%) of an oil. Mass spec. 337.2 (M-Boc)H+, 459.3 M Na+. NMR (CDCl$_3$), 7.2–7.6 (5H, M), 5.1–5.4 (3H, M), 3.9–4.4 (3H, M), 3.5–3.8 (1H, M), 3.1–3.5 (3H, M), 1.6–2.2 (2H, M), 1.4–1.5 (9H, S), 1.1–1.5 (7H, M), 0.8–1.0 (3H t).

c. 3-Butyl-2-oxo-4-((phenylmethoxy)-carbonyl)-piperazine

Intermediate 7b (7.10 g, 16.3 mmole) was dissolved in 25 ml of 9:1/Tfa:H$_2$O and stirred for 15 min. under nitrogen. Solvents were removed under reduced pressure, and the residue was taken up in EtOAc. The solution was washed with a saturated NaHCO$_3$ solution, dried over MgSO$_4$, filtered, and solvents were removed under reduced pressure. 10 ml acetic acid and 10 ml pyridine was added to the residue, and it was refluxed for 1 hour under nitrogen. Solvents were removed under reduced pressure, and the residue was dissolved in EtOAc and washed two times with 5% citric acid. The solution was dried over MgSO$_4$, filtered, and solvents were removed under reduced pressure. The product was crystallized from a solution of EtOAc/hexanes to yield 2.40 g (51%) of a white powder. m.r.=107–108° C. Mass spec. 291.2 MH+, 313.2 M Na+. NMR (CDCl$_3$), 7.3–7.5 (5H, S), 7.0–7.2 (1H, S br), 5.1–5.3 (2H, Q), 4.5–4.8 (1H, S br), 4.1–4.4 (1H, S br), 3.4–3.6 (1H, T), 3.1–3.4 (2H, D), 1.7–2.1 (2H, M), 1.2–1.5 (4H, M), 0.8–1.0 (3H S br).

d. 3-Butyl-4-((phenylmethoxy)-carbonyl)-2-thio-piperazine

Intermediate 7c (2.85 g, 9.83 mmole) and Lawsson's reagent (2.02 g, 5.00 mmole) were dissolved in 20 ml THF and heated at reflux under nitrogen for 1.5 hours. The solution was cooled, and solvents were removed under reduced pressure. The residue was dissolved in 50 ml Et$_2$O and washed three times with 25 ml of IN NaOH. The solution was dried over MgSO$_4$, filtered, and solvents were removed under reduced pressure. The residue was purified by flash chromatography on silica gel using 65:35/hexanes:EtOAc as an eluant. The product fractions were concentrated to yield 2.19 g (73%) of an oil which crystallized. m.r.=94–96° C. Mass spec. 307.2 MH+, 329.2 M Na+. NMR (CDCl$_3$), 8.5–8.8 (1H, S), 7.3–7.5 (5H, S br), 4.9–5.4 (3H, M), 4.0–4.5 (1H, M), 1.1–3.6 (3H, M), 3.4–3.6 (1H, T), 2.2–2.4 (2H, S br), 1.7–2.0 (2H, M), 1.2–1.6 (4H, S br), 0.7–1.0 (3H S br).

e. 8-Butyl-3-phenyl-7-((phenylmethoxy)-carbonyl)-5,6,7,8-tetrahydro-imidazo-[1,2a]-pyrazine Intermediate 7d (1.07 g, 3.5 mmole) was dissolved in 10 ml THF. Iodomethane (2.18 ml, 35.0 mmole) was added and stirred at room temperature for 8 hours. Solvents were removed under reduced pressure. The residue was dissolved in 10 ml THF, and 4-methylmorpholine (771 ul, 7.0 mmole) and 2-aminoacetophenone hydrochloride (686 mg, 4.00 mmole) were added to the solution. The solution was stirred overnight at room temperature and then refluxed for 2 hours. 15 ml acetic acid was added, and 15 ml solvent was distilled off. The solution was then refluxed for 1 hour and concentrated under vacuum. The residue was purified by flash chromatography on silica gel using 70:30/hexanes:EtOAc as an eluant. The product fractions were concentrated to yield 0.97g (71%) of an oil. Mass spec. 390.3 MH+, 412.2 M Na+. NMR (CD$_3$CO$_2$D), (approximately 1:1 mixture of conformers) 7.2–7.6 (11H, M), 5.6–5.8 (1H, M), 5.0–5.4 (2H, M), 4.4–4.8 (1H, M), 4.1–4.4 (1H, M), 3.9–4.1 (1H, M), 3.3–3.6 (1H, S br), 1.8–2.2 (obscured by solvent) (2H, M), 1.7–2.0 (2H, M), 1.1–1.6 (4H, S br), 0.7–0.9 (3H S br).

f. 8-Butyl-3-phenyl-5,6,7,8-tetrahydro-imidazo-[1,2a]-pyrazine

Intermediate 7e (1.08 g, 2.78 mmole) was dissolved in 4 ml of THF. 10 ml of 4N HCl was added, and the mixture was heated at reflux under nitrogen for 4 hours. Solvents were removed under reduced pressure to yield a solid product which was washed with ether and dried to 740 mg. Mass spec. 256 MH+.

g. 8-Butyl-7-(2-((1,1-dimethylethoxy-)carbonyl-)amino-1-oxo-3-(triphenylmethyl-thio)-propyl)-3-phenyl-5,6,7,8-tetrahydro-imidazo-[1,2a]-pyrazine Boc-Cys(Trt)-OH (2.32 g, 5.00 mmole; Advanced Chemtech) was dissolved in 20 ml of THF. DCC (515 mg, 2.50 mmole) was added to this solution. The solution was allowed to stand for 15 min., and the DCC was filtered off. The filtrate was added to a solution of intermediate 7f (700 mg, 2.4 mmole) and NMM (655 ul, 4.80 mmole) in 20 ml of THF. The solution was stirred for two hours at room temperature, and solvents were removed under reduced pressure. The resulting product was purified by silica gel chromatography using 70:30/hexanes:EtOAc as an eluant. The product fractions were combined and concentrated to a foam, which was dried to yield 1.47 g (87.5%) of product. Mass spec. 701.4 MH+, NMR (CD$_3$CO$_2$D), 7.1–7.7 (21H, M), 6.0–6.2 (1H, M), 6.5–6.7 (1H, T), 3.4–4.4 (4H, M), 2.4–2.8 (2H, M), 1.8–2.4 (2H, M) (partially obscured by solvent signal), 1.4 (9H, S), 1.1–1.4 (4H, M), 0.7–1.0 (3H, M)).

h. 7-Butyl-6-(2-((dimethylethoxy)-carbonyl-)amino-3-(triphenylmethyl-thio)propyl-)-3-phenyl-4,5,6,7-tetrahydro-imidazo-[1,2a]piperazine Intermediate 7g (350 mg, 0.50 mmole) was dissolved in THf (3 ml) and 1M BH$_3$/THf (7 ml, 7.0 mmole) was added. The reaction was heated at reflux for 2 hr under N$_2$. The solution was cooled to room temperature, and the excess reagent was destroyed by careful addition of a solution of MeOH (8 ml) and acetic acid (2 ml). The crude product was concentrated under reduced pressure and redissolved in 3:1/acetic acid:H$_2$) for 1 hr. After removing solvents under reduced pressure, the residue was purified by flash chromatography on silica gel using 1% HOAc/ETOAc as eluant. The product fractions were combined, concentrated, and dried to 100 mg (29%). MH+687.5.

i. 7-(2-amino-3-thio-propyl)-8-butyl-3-phenyl-5,6,7,8-tetrahydro-imidazo-[1,2a]-pyrazine (Compound 7)

Intermediate 7h (100 mg, 0.146 mmole) was treated under nitrogen with a mixture of Tfa:H2O:iPr$_3$SiH/93:5:2 (10 ml) for 15 min. Solvents were removed under reduced pressure, and the resulting solids were triturated eight times with 4 ml of H$_2$O and then filtered off. The filtrate was purified by prep HPLC to yield 45 mg (74%) of lyophilized compound 7 which appeared as a 1:1 mixture of isomers on analytical HPLC. Mass spec. 345.2 MH+, NMR (CD$_3$CO$_2$D), 7.4–7.7 (6H, M), 6.0–6.4 (1H, M), 3.8–5.3 (5H, M), 3.0–3.4 (2H, M), 2.0–2.4 (2H, M), 1.2–1.7 (4H, M), 0.9–1.0 (3H, M).

EXAMPLE 8

2-(1-(N-(2-Amino-1-oxo-3-thiopropyl)-N-methyl)-amino-pentyl)-5-phenyl-imidazole (Compound 8)

Compound 8 was synthesized according to Scheme 3 as set forth below:

SCHEME 3

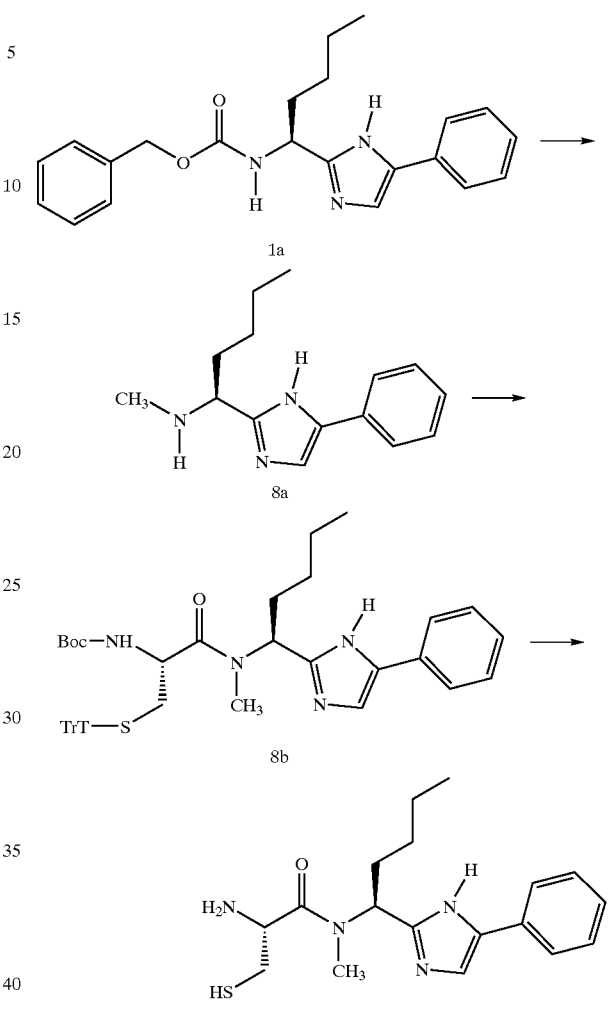

a. 5-(1-(Methylamino)-pentyl)-2-phenyl-imidazole

Intermediate 1a (1.50 g, 4.10 mmole) and LAH (50% in oil; Alfa Products, Danvers, Mass.) (1.25 g, 16.4 mmole) were combined in toluene (10 ml) and THF (5 ml) under nitrogen, and the mixture was heated to 55° C. for 4 hrs. The mixture was poured into EtOAc (100 ml), and moist celite was added to the mixture. Solids were filtered off, and the filtrate was dried over Na$_2$SO$_4$ and concentrated. The crude product was used without further purification.

b. 5-((N-(2-(((1,1-Dimethylethoxy-)carbonyl-)-amino)-1-oxo-3-(triphenylmethyl-thio)-propyl)-N-methyl-amino)-pentyl)-2-phenyl-imidazole Boc-Cys(Trt)-OH (3.8 g, 8.2 mmole) and DIC (643 ul, 4.1 mmole) were combined in CH$_2$Cl$_2$ (50 ml) and stirred for 0.5 hours at room temperature. Intermediate 8a (1.00 g, 4.1 mmole) was added and stirred at room temperature for 1 hour. Solids were filtered off and diluted to 100 ml with CH$_2$Cl$_2$. The solution was washed with saturated NaHCO$_3$ (3×50 ml) and saturated NaCl (1×50 ml), dried over Na$_2$SO$_4$, filtered, and concentrated. The residue was purified by flash chromatography on silica gel (120 g) using first CH$_2$Cl$_2$, and then 1% MeOH/CH$_2$Cl$_2$ as eluants. Product fractions were combined and concentrated to yield 1.36 g (46%) of product.

c. 2-(1-(N-(2-Amino-1-oxo-3-thiopropyl)-N-methyl)-amino-pentyl)-5-phenyl-imidazole (Compound 8)

Intermediate 8b was dissolved in 10 ml of Reagent B under nitrogen, and the solution was stirred for 0.5 hours. Solids were filtered off, and solvents were removed under a stream of nitrogen. The residue was triturated with ethyl ether and purified by reverse phase HPLC to yield compound 8 as a white solid after lyophilization (74.1 mg, 49%). Mass spec: 347.2 MH+.

EXAMPLE 9

2-(((2-Amino-1-oxo-3-mercapto-propyl)-amino)-methyl)-5-phenyl-thiazole-4-carbonyl-methionine (Compound 9)

Compound 9 was synthesized according to Scheme 4 as set forth below.

SCHEME 4

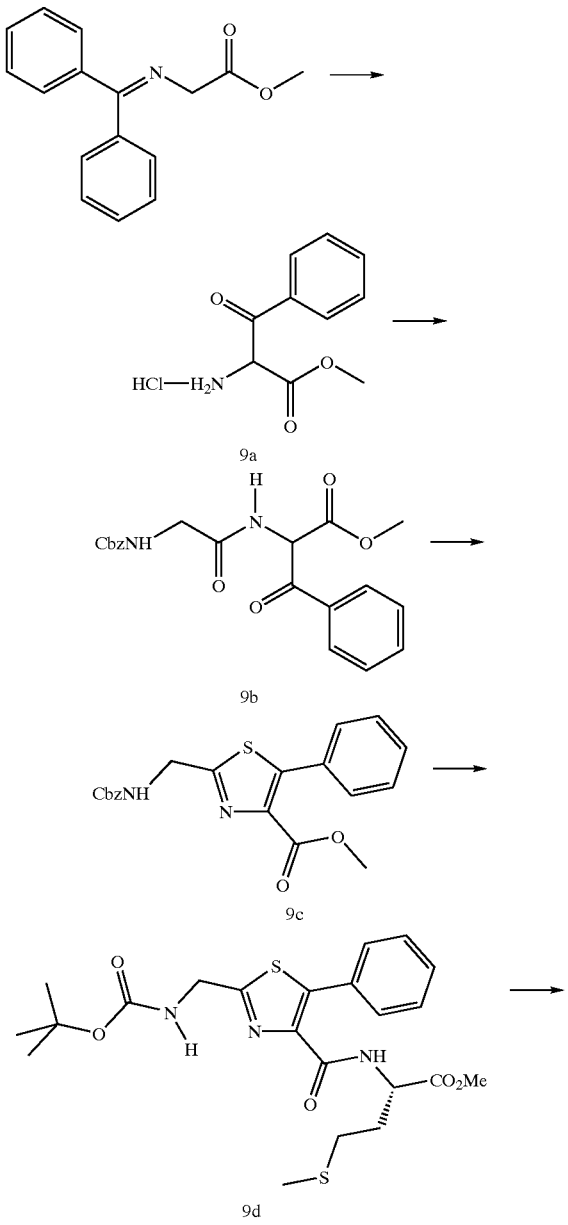

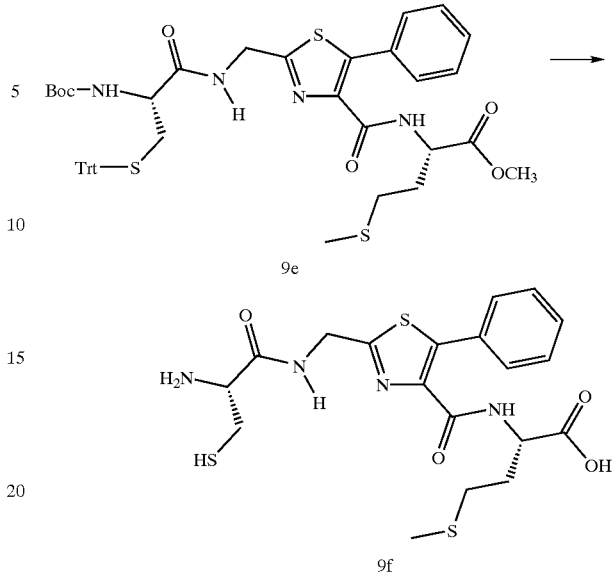

a. Methyl, 2-Amino-3-oxo-3-phenylpropionate

Schiff base (10.0 g, 39.5 mmole) was prepared as described in (O'Donnel, et al., J. Org. Chem. 47:2663 (1982). Schiff base was dissolved in THF (60 ml) and added dropwise to a stirred mixture of KOtBu (4.43 g, 39.5 mmole) in THF (30 ml) which was cooled to −70° C. under nitrogen. The solution was stirred for 10 min. at −70° C., and the anion was transferred to a stirred solution of benzoyl chloride (4.59 ml, 39.5 mmole) in THF (50 ml) which had also been cooled to −70° C. under nitrogen. The solution was stirred for 45 min. at −70° C. and then quenched by the addition of 4N HCl (30 ml). THF was removed under reduced pressure, and the aqueous layer was washed twice with 50 ml of ethyl ether. The solution was concentrated to a solid, and the product was dissolved in MeOH (30 ml), and the KCl was filtered. The product was crystallized by the addition of ether to the point of turbidity. The product was filtered off and dried to yield 2.89 g (32%) of product. Mass spec. 194.1 (MH+)

b. Methyl, 2-(((1,1-Dimethylethoxy-)carbonyl-)glycyl)-amino-3-oxo-3-phenylpropionate Boc-Gly-OH (3.15 g, 18.0 mmole) and NMM (1.98 ml, 18.0 mmole) were combined in THF (50 ml) and the solution was cooled to −20° C. iBuCOCl (2.34 ml, 18.0 mmole) was added to the solution, and the mixture was stirred for 5 min. at −20° C. Intermediate 9a (4.13 g, 18.0 mmole) and NMM (1.98 ml, 18.0 mmole) was added to the solution which was stirred vigorously while returning to room temperature. The solution was concentrated under reduced pressure, and the residue was dissolved in EtOAc (50 ml) and washed once with H$_2$O, once with 5% citric acid solution, and once with saturated NaCl solution. The solution was dried over MgSO$_4$, filtered, and concentrated under reduced pressure. Further purification was accomplished by flash chromatography on silica gel using 1:1/hexanes:EtOAc as an eluant. Product fractions were combined and concentrated to yield 3.28 g (52%) of product. Mass spec. 373.2 MNa+ c. Methyl, 2-(((1,1-Dimethylethoxy-)carbonyl-)-amino)-methyl-5-phenyl-thiazole-4-carboxylate Intermediate 9b (3.10 g, 8.86 mmole) and Lawesson's reagent (3.6 g, 8.9 mmole; Aldrich Chem. Co., St. Louis, Mo.) were combined in THF (30 ml) and heated to reflux for 1 hour. Solvents were removed under a stream of nitrogen, and the residue was purified by flash chromatography on silica gel using 1:1/hexanes:EtOAc as an eluant. Product fractions were combined and concentrated under reduced pressure to yield 2.21 g (72%) of product. Mass spec. 349.0 MH+, 371.2 MNa+.

d. 2-(((1,1-Dimethylethoxy-)carbonyl-)-amino)-methyl-5-phenyl-thiazole-4-carbonyl-methionine Methyl Ester Intermediate 9c was dissolved in methanol (5 ml), and an aqueous solution of NaOH (344 mg, 8.61 mmole) in minimum of $H_2O$ was added to the solution. The solution was stirred at 40° C. for 1 hour, and the solvents were removed under reduced pressure. The residue was distributed between EtOAc (20 ml) and 5% citric acid (20 ml). The EtOAc layer was dried over $MgSO_4$, filtered, and concentrated under reduced pressure. The residue was dissolved in THF (10 ml), and HOSu (330 mg, 2.87 mmole), HCl-MetOMe (573 mg, 2.87 mmole), 30 NMM (316 mg, 2.87 mmole) and DCC (591 mg, 2.87 mmole) were added to the solution. The mixture was stirred at room temperature overnight, filtered, and concentrated under reduced pressure. The residue was taken up in EtOAc (25 ml), and washed once in 5% citric acid solution and twice in a saturated $NaHCO_3$ solution. The solution was dried over $MgSO_4$, filtered, and concentrated under reduced pressure to yield 590 mg (43%) of product. Mass spec. 502.2 MNa+, 480.4 MH+ e. 2-(((2-(((1,1-Dimethylethoxy)-carbonyl)-amino)-1-oxo-3-(triphenylmethyl-thio)-propyl)-amino)-methyl)-5-phenyl-thiazole-4-carbonyl-methionine Methyl Ester Intermediate 9d (590 mg, 1.23 mmole) was treated with Reagent B (10 ml) for 15 min at room temperature under nitrogen. Solvents were removed under reduced pressure. The residue was triturated twice with 25 ml $Et_2O$ and decanted. The residue was then dissolved in THF (10 ml) and added to the mixed anhydride generated from Boc-Cys (Trt)-OH (570 mg, 1.23 mmole), NMM (135 ul. 1.23 mmole) and iBuOCOCl (160 ul, 1.23 mmole) at −20° C. under nitrogen over 5 min. NMM (135 ul, 1.23 mmole) was added to the mixture which was then allowed to warm to room temperature. Solvents were removed under reduced pressure. The residue was taken up in EtOAc (25 ml) and washed with 25 ml of $H_2O$ and 25 ml of 5% citric acid solution. The solution was dried over $MgSO_4$ and concentrated to yield 1.01 g (100%) of a white foam.

f. 2-(((2-Amino-1-oxo-3-mercapto-propyl)-amino)-methyl)-5-phenyl-thiazole-4-carbonyl-methionine (Compound 9)

Intermediate 9e (250 mg, 0.30 mmole) was dissolved in MeOH (2 ml). NaOH (40 mg), dissolved in a minimum of $H_2O$, was added to the solution. The solution was stirred overnight at room temperature. Solvents were removed under reduced pressure and the residue was dissolved in reagent B (10 ml). The solution was stirred for 15 min. at room temperature under nitrogen and then concentrated under reduced pressure. The residue was purified by reverse phase HPLC. Product fractions were combined and lyophilized to yield 32 mg (20%) of compound 9 as a white solid. Mass spec 469 MH+.

EXAMPLE 10 bis-1,1'-[2-Amino-3-(8-butyl-2-(2-methoxyphenyl)-5,6,7,8-tetrahydro-imidazo[1,2a]pyrazine-6-yl)-3-oxo]propyl Disulfide (Compound 10)

Intermediate 3e (300 mg, 0.41 mmole) was dissolved in methanol, and $H_2O$ (0.3 ml) was added. A solution of iodine (104 mg, 0.41 mmol) in methanol (3 ml) was added, and the mixture was stirred for 2 hours. The solvents were removed under reduced pressure, and the residue was triturated with hexanes (2×5 ml). The residue was then dissolved in ETOAc (5 ml) and washed with 5% $Na_2S_2O_3$ solution (10 ml). The organic layer was dried over $Na_2SO_4$, filtered, and concentrated to a glass.

The glass was treated with 93:5:2/Tfa:$H_2O$:iPr$_3$SiH for 15 minutes under $N_2$. The solvents were removed under reduced pressure, and the residue was purified by RP HPLC and lyophilized. Yield=48 mg (25%). Mas spec. 775.4 MH+, 388.5 $M^2H^{++}$, NMR (DMSO-d$_6$), (approx. 5:1 mixture of conformers) 8.5–9.0 (3H,S), 8.0–8.2 (1H,d), 7.5–7.7 (1H,S), 7.1–7.3 (1H,t), 7.0–7.1 (1H,d), 6.9–7.1 (1H, t), 5.2–5.6 (1H,t), 4.8–5.0 (1H,t), 3.6–4.7 (1H,M), 3.8–4.0 (3H,S), 3.2–3.5 (2H,M), 1.8–2.2 (2H,M), 1.2–1.7 (4H, M), 0.8–1.0 (3H, t).

EXAMPLE 11

7-(2-Amino-1-oxo-3-thio-propyl)-2-(2-methoxyphenyl)-8-(2-methylpropyl)-5,6,7,8-tetrahydro-imidazo-[1,2a]-pyrazine (Compound 11)

Compound 11 was prepared in a manner analogous to Example 3 except Boc-L-Leucine was used in place of Cbz-(L)-Norleucine in step a and the Boc group was cleaved with a 9:1/Tfa:H2) mixture instead of by catalytic hydrogenation in step c. Mass spec. 389.1 MH+. NMR (300 MHz, DMSO-d$_6$) 8.6–8.8 (3H, s), 8.1–8.2 (1H, d), 7.9–8.1 (1H, S), 7.3–7.5 (1H, t), 7.1–7.3 (1H, d), 7.0–7.1 (1H, T), 5.9–6.1 (1H, d), 4.7–4.8 (1H, S), 4.5–4.7 (1H, d), 4.3–4.4 (1H, d), 4.1–4.3 (1H, t), 3.9–4.0 (3H, S), 3.8–4.0 (1H, T), 3.3–3.5 (1H, t), 2.8–3.1 (2H, M), 1.9–2.2 (2H, M), 1.7–1.8 (1H, M), 1.0–1.2 (3H, t), 0.8–1.0 (3H, t).

EXAMPLE 12 bis-1,1'-[2-Amino-3-(2-(2-methoxyphenyl)-8-(2-methylpropyl)-5,6,7,8-tetrahydro-imidazo[1,2a]piperazine-7-yl)-3-oxo]propyl Disulfide (Compound 12)

Compound 12 was prepared in a manner analogous to Example 10 except intermediate 11e was used in place of intermediate 3e. Mass. spec 388.5 M2H++, 775.4 MH+. NMR (300 MHz, DMSO-d$_6$) 8.7–9.2 (3H, S), 8.1–8.2 (1H, d), 7.9–8.1 (1H, S), 7.3–7.5 (1H, t), 7.1–7.3 (1H, d), 7.0–7.2 (1H, t), 5.9–6.1 (1H, d), 4.8–5.0 (1H,S), 4.5–4.7 (1H, d), 4.3–4.5 (1H, d), 4.1–4.4 (1H, t), 3.8–4.1 (1H,M), 3.8–4.0 (3H, S), 3.2–3.5 (2H, M), 1.8–2.2 (2H, M), 1.7–1.9 (1H, M), 1.0–1.2 (3H, d), 0.8–1.0 (3H, d).

EXAMPLE 13

7-(2-Amino-1-oxo-3-thiopropyl)-8-butyl-2-(2-ethoxyphenyl)-5,6,7,8-tetrahydroimidazo[1,2a]pyrazine (Compound 13).

a. Intermediate 3c (2.54 g, 8.50 mMole) was dissolved in THF (15 ml) and a 1M solution of borane in THF (34.0 ml, 34.0 mMole) was added dropwise over 10 minutes at room temperature. The mixture was refluxed for 2 hours and allowed to stand at room temperature overnight. A solution of 4 N HCl (25 ml) was added dropwise and the resulting mixture was heated at reflux for a hour. The mixture was concentrated to $H_2O$, made basic by careful addition of solid $NaHCO_3$, and extracted with EtOAc (2×25 ml). The EtOAc layers were dried over $Na_2SO_4$, filtered, and concentrated to an oil. A solution of 5% HCl (25 ml) was added, and the mixture was concentrated to a solid. The solid was recrystallized from methanol and ethyl ether to yield 2.72 g (89.5%) of the dihydrochloride salt. Mass spec. 286.2. M.R.=242–247° C.

b. Intermediate 13a (850 mg, 2.37 mMole) was distributed between $CH_2Cl_2$ and saturated $NaHCO_3$ solution, the $CH_2Cl_2$ layer was dried over $Na_2SO_4$, and filtered. A 1M solution of $BBr_3$ in $CH_2Cl_2$ was added and the resulting mixture was heated at reflux for 1 hour. The reaction was cooled and poured onto saturated $NaHCO_3$ solution (25 ml). The $CH_2Cl_2$ layer was dried over $Na_2SO_4$ and filtered. Di-(tert)-butyldicarbonate (523 mg, 2.40 mMole) was added and the mixture was stirred at room temperature over the weekend. Solvents were evaporated, and the resulting oil was purified by column chromatography on silica gel using 70:30/hexanes: Ethyl acetate as eluant. Yield=700 mg (80%) of a clear oil. Mass spec. 372.2 (MH+). NMR c. Protected intermediate (13b) (600 mg, 1.62 mMole) was dissolved in THF (10 ml) and added dropwise to a solution of NaH (60% in oil, 120 mg, 3.0 mMole) in THF (10 ml) at room temperature under $N_2$. The reaction was stirred 15 minutes and ethyl iodide (400 ul, 5.00 mMole) was added. The mixture was stirred overnight at room temperature then concentrated under reduced pressure. Saturated $NaHCO_3$ solution (10 ml) was added, and the product was extracted with ethyl ether (2×20 ml). The ether was evaporated, and the residue was purified by column chromatography on silica gel using 3:1/hexanes: ethyl acetate as eluant. Yield= 410 mg (64%) of the ether. Mass spec. 400.3 (MH+). M.R.=103–109° C.

d. Intermediate (13c) was treated with 90% $TFA/H_2O$ (2 ml) for 0.5 hours and concentrated to remove the BOC group. Coupling with Boc-(L)-Cys(Trt)-OH and deprotection were accomplished in a manner analogous to example 1e and 1f, respectively, to yield compound 13. Mass spec. 403.2 (MH+). NMR (300 MHz, DMSO-d6) 8.4–8.7 (3H, broad s), 7.9–8.0 (1H, s), 7.75–7.9 (1H, d), 7.15–7.3 (1H, t), 7.0–7.1 (1H, d), 6.85–7.0 (1H, t), 5.7–5.85 (1H, m), 4.65–4.8 (1H, broad s), 4.45–4.6 (1H, d), 4.3–4.4 (1H, d,d), 4.1–4.25 (1H, m), 3.75–3.95 (1H, m), 3.1–3.3 (1H, m), 2.8–3.1 (2H, m), 1.9–2.15 (2H, m), 1.2–1.5 (4H, m), 0.8–1.0 (3H, t).

EXAMPLE 14

7-(2-Amino-1-oxo-3-thiopropyl)-8-butyl-2-(2-hydroxyphenyl)-5,6,7,8-tetrahydroimidazo[1,2a]pyrazine (Compound 14).

a. Intermediate 13a (179 mg, 0.50 mMole) was distributed between $CH_2Cl_2$ and saturated $NaHCO_3$ solution, the $CH_2Cl_2$ layer was dried over $Na_2SO_4$, and filtered. A 1M solution of $BBr_3$ in $CH_2Cl_2$ was added, and the resulting mixture was heated at reflux for 1 hour. The reaction was cooled and poured onto saturated $NaHCO_3$ solution (25 ml). The $CH_2Cl_2$ layer was dried over $Na_2SO_4$, filtered, and stripped to yield crude de-methylated product as a gum. This material was used without further purification.

b. Coupling of (14a) with Boc-(L)-Cys(Trt)-OH and deprotection were accomplished in a manner analogous to example 1e and 1f, respectively, to yield compound 14. Mass spec. 403.2 (MH+). NMR (300 MHz, DMSO-d6) 8.55–8.8 (3H, broad s), 8.1–8.2 (1H, d), 7.85–7.95 (1H, s), 7.35–7.45 (1H, t), 7.15–7.25 (1H, d), 7.0–7.15 (1H, t), 5.85–6.0 (1H, d,d), 4.65–4.8 (1H, broad s), 4.55–4.7 (1H, d,d), 4.15–4.3 (2H, q), 4.1–4.2 (1H, m), 3.8–3.95 (1H, m), 3.3–3.5 (1H, t), 2.15–2.3 (1H, m), 1.95–2.15 (1H, m), 1.4–1.5 (3H, t), 1.2–1.5 (4H, m), 0.8–1.0 (3H, t).

EXAMPLE 15

2-(1-(N-(2-Amino-1-oxo-3-thiopropyl)-N-Methyl)-amino-pentyl-5-(2-methoxyphenyl)-imidazole (Compound 15)

Compound 15 was prepared in a manner analogous to example 8 except 2-Bromo-2'-methoxyacetophenone was used in place of 2-Bromoacetophenone in step 1a. Mass Spec. 377.1 MH+. NMR (300 MHz, CD3CO2D) 7.8–7.9 (1H, s), 7.65–7.75 (1H, d,d), 7.4–7.55 (1H, m), 7.14–7.2 (1H, d), 7.05–7.14 (1H, t), 5.6–5.8 (1H, t), 4.8–4.9 (1H, t), 3.9–4.0 (3H, s), 3.25–3.35 (3H, s), 3.05–3.25 (2H, m), 2.2–2.4 (2H, m), 1.2–1.6 (4H, m), 0.8–1.0 (3H, t).

EXAMPLE 16 bis-1,1'-[2-(1-(N-(2-Amino-1-oxo-3-thiopropyl)-N-methylamino)-pentyl]-5-(2-methoxyphenyl)imidazole]disulfide (Compound 16)

Compound 16 was prepared in a manner analogous to example 10 except compound-15 in place of intermediate 3e. Mass spec. 751.5 MH+. NMR (300 MHz, CD3CO2D) 7.75–7.85 (1H, s), 7.65–7.75 (1H, d,d), 7.35–7.5 (1H, m), 7.1–7.2 (1H, d), 7.0–7.1 (1H, t), 5.5–5.6 (1H, t), 4.8–4.95 (1H, t), 3.9–4.1 (3H, s), 3.3–3.5 (2H, m), 3.2–3.3 (1H, s), 2.2–2.4 (2H, m), 2.0–2.2 (acetate signal), 1.2–1.6 (4H, m), 0.8–1.0 (3H, t).

EXAMPLE 17

7-(2-Amino-1-oxo-3-thiopropyl)-8-(2-methylpropyl)-2-(1-naphthyl)-5,6,7,8-tetrahydroimidazo[1,2a]pyrazine (Compound 17).

a. 1'-Acetonaphthone (10.2 g, 60.0 mMole) and 0.1 ml of concentrated HCl were dissolved in acetic acid (100 ml) and bromine (9.6 g, 60.0 mMole) were added dropwise with stirring over a three hour period. The reaction was concentrated under reduced pressure and dried to constant weight. The product was used without further purification.

b. Compound 17 was prepared in a manner analogous to example 1 except Cbz-(L)-Leucine was used in place of Cbz-(L)-Norleucine, intermediate 17a was used in place of 2-Bromoacetophenone in step 1a, and 1M $BH_3$/THF was used for reduction of lactam intermediate in step d. Mass spec. 409.2 MH+. NMR (300 MHz, DMSO-d6) 8.5–8.9 (3H, s), 8.1–8.25 (1H, d), 7.9–8.15 (3H, m), 7.7–7.8 (1H, d), 7.5–7.7 (3H, m), 5.8–6.1 (1H, d), 4.7–4.85 (1H, s), 4.55–4.75 (1H, d), 4.2–4.45 (2H, m), 3.85–4.05 (1H, m), 3.0–3.4 (10H, H2O), 2.9–3.1 (2H, q), 1.9–2.2 (1H, t), 1.7–1.9 (2H, m), 1.0–1.2 (3H, d), 0.8–1.0 (3H, d).

EXAMPLE 18

7-(2-Amino-1-oxo-3-thiopropyl)-8-(1-methylpropyl)-2-(2-methoxyphenyl)-5,6,7,8-tetrahydroimidazo[1,2a]pyrazine (Compound 18).

Compound 18 was prepared in a manner analogous to example 3 except Cbz-(L)-Isoleucine was used in place on Cbz-(L)-Norleucine in step a. Mass spec. 389.3 MH+. NMR (300 MHz, DMSO-d6) 8.5–8.9 (3H, s), 8.05–8.2 (1H, d), 7.9–8.05 (1H, s), 7.35–7.5 (1H, t), 7.15–7.25 (1H, d), 7.0–7.15 (1H, t), 5.65–5.85 (1H, d), 4.65–4.8 (1H, s), 4.5–4.65 (1H, d,d), 4.3–4.45 (1H, d,d), 3.9–4.0 (3H, s), 3.8–4.0 (1H, m), 3.2–3.7 (8H, H20), 2.8–3.0 (2H, m), 2.2–2.4 (1H, m), 1.4–1.6 (1H, m), 1.15–1.35 (1H, m), 1.0–1.15 (3H, d), 0.8–0.95 (3H, t).

EXAMPLE 19 bis-1,1'-7-(2-Amino-1-oxo-3-thiopropyl-(2-(1-naphthyl)-8-(2-methylpropyl)-5,6,7,8-tetrahydroimidazo[1,2a]pyrazin-7-yl) disulfide (Compound 19).

Compound 19 was prepared in a manner analogous to example 10 except compound 17 was used in place of intermediate 3e. Mass spec. 815.5 MH+. NMR (300 MHz, DMSO-d6) 8.7–9.2 (3H, s), 8.15–8.3 (1H, s), 8.0–8.1 (2H, m), 7.85–8.0 (1H, s), 7.7–7.8 (1H, d), 7.5–7.7 (3H, m), 5.8–6.0 (1H, s), 4.8–5.0 (1H, s), 4.5–4.54 (1H, d), 4.4–4.5 (1H, d), 4.2–4.4 (1H, t), 3.9–4.1 (1H, t), 3.0–3.9 (12H, m H2O obscures signal), 2.0–2.2 (1H, t), 1.7–2.0 (2H, m), 1.0–1.2 (3H, d), 0.85–1.0 (3H, d).

EXAMPLE 20 bis-1,1'-[7-(2-Amino-1-oxo-3-thiopropyl)-2-(methoxy-phenyl)-8-(1-methylpropyl)-5,6,7,8-tetrahydroimidazo[1,2a]pyrazine]disulfide (Compound 20).

Compound 20 was prepared in a manner analogous to example 10 except compound 18 was used in place of intermediate 3e. Mass spec. 775.5 MH+. NMR (300 MHz, DMSO-d6) 8.7–9.0 (3H, s), 8.05–8.15 (1H, d), 7.9–8.1 (1H, s), 7.35–7.5 (1H, t), 7.15–7.25 (1H, d), 7.0–7.15 (1H, t), 5.65–5.85 (1H, d), 4.8–5.0 (1H, s), 4.45–4.6 (1H, d), 4.35–4.5 (1H, d), 4.2–4.35 (1H, m), 3.8–4.1 (1H, m), 3.8–3.9 (3H, s), 3.4–3.8 (10H, H2O), 3.2–3.4 (2H, d), 2.2–2.4 (1H, m), 1.4–1.65 (1H, m), 1.15–1.35 (1H, m), 1.0–1.15 (3H, d), 0.8–0.95 (3H, t).

EXAMPLE 21

S-(Dimethylethyl)-S'-[2-amino-3-oxo-3(8-butyl-2-(2-methoxyphenyl;)-5,6,7,8-tetrahydroimidazo[1,2a]pyrazin-7-yl)propyl]disulfide (Compound 21)

Compound 21 was prepared in a manner analogous to example 3 except that Fmoc-(L)-Cys(tBuS-)OH was used in step e and final deprotection was accomplished by treatment with tris(aminoethyl)amine (1.5 ml per mmole) in $CH_2Cl_2$ (10 ml per mmole) for 0.5 hour at room temperature. The product was purified by preparative reverse phase column chromatography to provide pure compound 21. Mass spec. 477.3 MH+. NMR (300 MHz, DMSO-d6, 90° C.) 8.0–8.1 (1H, d), 7.4–7.5 (1H, s), 7.1–7.3 (1H, t), 7.0–7.1 (1H, d), 6.9–7.0 (1H, t), 5.4–5.55 (1H, s), 4.3–4.7 (1H, m), 4.1–4.3 (1H, d), 3.8–4.1 (7H, m), 3.0–3.2 (2H, m+H2O), 2.8–2.9 (1H, d,d), 2.1–2.3 (2H, m), 1.7–2.1 (2H, m), 1.2–1.7 (13H, m), 0.8–1.0 (3H, t).

EXAMPLE 22

7-(2-Amino-1-oxo-3-thiopropyl)-8-butyl-2-(2-methylphenyl)-5,6,7,8-tetrahydroimidazo[1,2a]pyrazine (Compound 22)

a. 2'-Methylacetophenone (25.0 g, 186 mMole) was dissolved in glacial acetic acid (250 ml) and concentrated HCl (250 uL) was added followed by a dropwise addition of bromine (9.6 ml, 186 mMole) over 15 minutes. The mixture was stirred 3 hours and then concentrated under reduced pressure. The residue was taken up in ethyl ether and washed with saturated $NaHCO_3$ solution. The ether layer was dried over $Na_2SO_4$, filtered, and concentrated to yield 38.0 g, (96%) of crude 2-bromo-2'-methylacetophenone which was used without further purification.

b. Compound 22 was prepared in a manner analogous to example 3 except 2-bromo-2'-methylacetophenone was used in place of 2-bromo-2'-methoxyacetophenone in step a. Mass spec. 373.2 MH+. NMR (300 MHz, DMSO-d6) 8.6–8.8 (3H, s), 7.9–8.0 (1H, s), 7.6–7.75 (1H, d), 7.3–7.5 (3H, m), 5.8–6.0 (1H, d,d), 4.7–4.8 (1H, s), 4.55–4.7 (1H, d), 4.3–4.44 (1H, d,d), 4.1–4.3 (1H, m), 3.8–4.0 (1H, m), 3.4–3.55 (1H, t), 2.85–3.1 (2H,-m), 2.4–2.5 (3H, s), 2.0–2.3 (2H, m), 1.2–1.6 (4H, m), 0.8–1.0 (3H, t).

EXAMPLE 23 bis-1,1'-[7-(2-Amino-1-oxo-3-thiopropyl)-8-butyl-2-(2-methylphenyl)-5,6,7,8-tetrahydroimidazo[1,2a]pyrazine]disulfide (Compound 23)

Compound 23 was prepared in a manner analogous to example 10 except compound 23 was used in place of intermediate 3e. Mass spec. 743.4 MH+. NMR (300 MHz, DMSO-d6, 90° C.) 7.6–7.8 (1H, d), 7.2–7.3 (1H, s), 7.0–7.2 (3H, m), 5.3–5.6 (1H, broad s), 4.3–4.8 (1H, broad s), 3.5–4.2 (4H, m), 3.0–3.3 (2H, broad s), 2.8–3.0 (1H, m), 2.4–2.5 (3H, s), 2.1–2.4 (2H, broad s), 1.7–2.1 (2H, m), 1.2–1.7 (4H, m), 0.8–1.0 (3H, t).

EXAMPLE 24

7-(2-Amino-1-oxo-3-thiopropyl)-8-(1,1-dimethylethyl)-2-(2-methoxyphenyl)-5,6,7,8-tetrahydroimidazo-[1,2a]pyrazine (Compound 24)

Compound 24 was prepared in a manner analogous to example 3 except Boc-(L)-t-Leucine was used in place of Cbz-(L)-Norleucine in step a and deprotection was accomplished in step c by treatment with trifluoroacetic acid for 0.5 hours. Mass spec. 389.3 MH+. NMR (300 MHz, DMSO-d6) 8.5–8.8 (3H, broad s), 7.95–8.1 (1H, d), 7.9–8.0 (1H, s), 7.3–7.5 (1H, t), 7.1–7.25 (1H, d), 7.0–7.15 (1H, t), 5.55–5.7 (1H, s), 4.65–4.8 (1H, broad s), 4.5–4.6 (1H, m), 4.35–4.5 (1H, m), 4.1–4.3 (1H, m), 3.9–4.1 (1H, m), 3.85–3.95 (3H, s), 3.3–3.4 (1H, t), 2.7–34.1 (2H, m), 1.0–1.2 (9H, s).

EXAMPLE 25

7-(2-Amino-1-oxo-3-thiopropyl)-8-(1-methylpropyl)-2-(2-(phenylmethoxy)phenyl)-5,6,7,8-tetrahydroimidazo[1,2a]pyrazine (Compound 25)

a. Intermediate 18d (3.36 g, 11.8 mMole) was dissolved in 10 ml $CH_2Cl_2$ and a 1M solution of $BBr_3$ in $CH_2Cl_2$ (47 ml) was added dropwise. The mixture was heated at reflux for 2 hours, cooled and poured into saturated $NaHCO_3$ solution (25 ml). The aqueous layer was extracted 3 times with $CH_2Cl_2$ (60 ml), dried over $Na_2SO_4$, filtered, and concentrated to 30 ml. Di-(tert) butyldicarbonate (2.57 g, 11.8 mMole) was added, and the reaction stirred at room temperature overnight. The crude product was purified by column chromatography on silica gel using 1:1/ethyl acetate:hexanes as eluant. The yield was 3.31 g (75%) of white solid product.

b. Intermediate 25a (850 mg, 2.29 mMole) was dissolved in THF (20 ml) that contained sodium hydride (96.1 mg, 2.4 mmole) and the mixture was treated with benzyl bromide (292 uL, 2.4 mMole) under $N_2$ at room temperature. The reaction was stirred overnight at room temperature and concentrated. The residue was partitioned between $CH_2Cl_2$ (30 ml) and $H_2O$ (15 ml). The $CH_2Cl_2$ layer was dried over $Na_2SO_4$, filtered, and concentrated. Crystallization from ethyl ether and hexanes yielded 887 mg (83.7%) of the product.

c. Intermediate 25b (887 mg, 1.92 mMole) was treated with 90% Tfa/H$_2$O (50 ml) for 15 minutes at room temperature under N$_2$. Solvents were removed under reduced pressure and the residue was distributed between CH$_2$Cl$_2$ and saturated NaHCO$_3$ solution. The CH$_2$Cl$_2$ layer was dried over Na$_2$SO$_4$ solution, filtered and concentrated. The crude intermediate was acylated in a manner analogous to example 1, step 1e, and then deprotected in a manner analogous to example 1, step f. Mass spec. 465.3 MH+. NMR (300 MHz, DMSO-d6) 8.3–8.8 (3H, braod s), 8.0–8.1 (1H, d,d), 7.8–8.0 (1H, s), 7.45–7.55 (2H, m), 7.3–7.45 (4H, m), 7.15–7.3 (1H, d), 7.0–7.15 (1H, t), 5.6–5.8 (1H, d), 5.3–5.4 (2H, s), 4.65–4.8 (1H, broad s), 4.45–4.6 (1H, m), 4.25–4.4 (1H, m), 4.1–4.25 (1H, m), 3.75–3.95 (1H, m), 3.25–3.4 (1H, t), 2.8–3.0 (2H, m), 2.15–2.4 (1H, m), 1.4–1.6 (1H, m), 1.1–1.35 (1H, m), 0.95–1.1(3H, d), 0.8–1.0 (3H, t).

EXAMPLE 26

7-(2-Amino-1-oxo-3-thiopropyl)-8-(cyclohexyl-methyl)-2-(2-methoxyphenyl)-5,6,7,8-tetrahydroimidazo[1,2a]pyrazine (Compound 26)

a. A solution of H-(L)-Phe-OH (10.0 g, 60.6 mMole) in acetic acid (60 ml) and 5% aqueous HCl (60 ml) was hydrogenated over PtO$_2$ (430 mg) until hydrogen was no longer consumed. Solvents were removed under reduced pressure, and the residue was dissolved in methanol (50 ml) and H$_2$O (20 ml). A 10% NaOH solution was added with vigorous stirring to pH=4.4, the solution was cooled, and the product was filtered off and washed with H$_2$O.

b. Crude intermediate 26a (60.6 mMole) was suspended in 100 ml H$_2$O containing K$_2$CO$_3$ (8.36 g, 60.6 mMole), and a solution of Cbz-Osu (15.1 g, 60.6 mMole) in CH$_3$CN (150 ml) was added with vigorous stirring for 45 minutes at room temperature. The CH$_3$CN was distilled off at reduced pressure and the aqueous layer was washed with ethyl ether. The aqueous layer was acidified with concentrated HCl to pH=1 and the product extracted with ethyl acetate (2×50 ml). The ethyl acetate layers were dried over Na$_2$SO$_4$, filtered, and concentrated under reduced pressure to yield 17.27 g (93%) of Cbz-(L)-cyclohexylalanine (26b).

c. Compound 26 was prepared in a manner analogous to example 3 except Cbz-(L)-Cyclohexylalanine (26b) was used in place of Cbz-(L)-Norleucine in step a. Mass spec. 429.3 (MH+). NMR (300 MHz, DMSO-d6) 8.6–8.9 (3H, s), 8.1–8.3 (1H, d,d), 7.9–8.1 (1H, s), 7.35–7.5 (1H, m), 7.15–7.25 (1H, d), 7.05–7.15 (1H, t), 6.0–6.1 (1H, t), 4.7–4.8 (1H, m), 4.55–4.7 (1H, m), 4.3–4.45 (1H, m), 4.1–4.3 (1H, m), 3.9–4.0 (3H, s), 3.8–3.95 (1H, m), 3.35–3.5 (1H, t), 2.8–3.1 (2H, m), 2.05–2.2 (1H, d), 1.9–2.1 (2H, t), 0.8–1.7 (10H, m).

EXAMPLE 27

7-(2-Amino-1-oxo-3-thiopropyl)-2-(2-methoxyphenyl)-8-(1-methylethyl)-5,6,7,8-tetrahydroimidazo[1,2a]pyrazine (Compound 27)

Compound 27 was prepared in a manner analogous to example 3 except Cbz-(L)-Valine was used in place of Cbz-(L)-Norleucine in step a. Mass spec. 375.1 MH+. NMR (300 MHz, DMSO-d6) 8.6–8.8 (3H, broad s), 8.1–8.3 (1H, d), 8.0–8.1 (1H, s), 7.35–7.5 (1H, t), 7.15–7.25 (1H, d), 7.05–7.15 (1H, t), 5.6–5.8 (1H, d), 4.65–4.8 (1H, broad s), 4.5–4.7 (1H, m), 4.3–4.45 (1H, m), 4.1–4.3 (1H, m), 3.9–4.0 (3H, s), 3.8–3.95 (1H, m), 3.35–3.5 (1H, t), 2.8–3.05 (2H, m), 2.5–2.7 (1H, m), 1.1–1.2 (3H, d), 0.9–1.05 (3H, d).

EXAMPLE 28 bis-1,1'-[7-(2-Amino-1-oxo-3-thiopropyl)-2-(2-methoxyphenyl)-8-(1-methylethyl)-5,6,7,8-tetrahydroimidazo[1,2a]]pyrazine]disulfide (Compound 28).

Compound 28 was prepared in a manner analogous to example 10 except compound 27 was used in place of intermediate 3e. Mass spec. 747.4 MH+. NMR (300 MHz, DMSO-d6) 8.8–9.0 (3H, broad s), 8.05–8.2 (1H, d), 7.9–8.1 (1H, s), 7.35–7.5 (1H, t), 7.15–7.25 (1H, d), 7.0–7.15 (1H, t), 5.55–5.75 (1H, broad s), 4.8–5.0 (1H, broad s), 4.45–4.65 (1H, m), 4.35–4.5 (1H, m), 4.2–4.35 (1H, m), 3.85–3.95 (3H, s), 3.9–4.05 (1H, m), 3.2–3.4 (2H, d), 2.45–2.65 (1H, m partially obscured by solvent), 1.05–1.2 (3H, d), 0.9–1.05 (3H, d).

EXAMPLE 29

7-(2-Amino-1-oxo-3-thiopropyl)-8-butyl-2(2-hydroxy-6-methoxyphenyl)-5,6,7,8-tetrahydro[1,2a]pyrazine (Compound 29)

a. Bromine (3.19 ml, 61.9 mMole) was added dropwise to a mixture of 2',6'-dimethoxysacetophenone (11.15 g, 61.9 mMole) and concentrated HCl (100 uL) in acetic acid (50 mL) over 20 minutes. The reaction was stirred at room temperature for 2 hours, and the solvents were evaporated under reduced pressure. The residue was dissolved in ethyl acetate (100 ml) and washed with saturated NaHCO$_3$ solution (100) and with saturated NaCl solution (100 ml). The ethyl acetate layer was dried over Na$_2$SO$_4$, filtered, and concentrated to an oil (14.9 g). Crystallization from ethyl acetate and hexanes yields 4.87 g (30%) of 2-bromo-2',6'-dimethoxyacetophenone (29a).

b. Compound 29 was prepared in a manner analogous to example 3 except 2-bromo-2',6'-dimethoxyacetophenone (29a) was used in place of 2-bromoacetophenone in step a. One methyl ether group is cleaved efficiently during BH$_3$ reduction of lactam 29d. Mass spec. 405.3.

EXAMPLE 30 bis-1,1'-[7-(2-Amino-1-oxo-3-thiopropyl)-8-(1,1-dimethylethyl)-2-(2-methoxyphenyl)-5,6,7,8-tetrahydroimidazo[1,2a]pyrazine]disulfide (Compound 30)

Compound 30 was prepared in a manner analogous to example 10 except compound 24 was used in place of intermediate 3e. Mass spec. 775.5 (MH+). NMR (300 MHz, DMSO-d6) 8.7–9.1 (3H, broad s), 8.0–8.1 (1H, d), 7.8–8.0 (1H, s), 7.3–7.5 (1H, t), 7.1–7.2 (1H, d), 7.0–7.1 (1H, t), 5.55–5.65 (1H, s), 4.8–5.0 (1H, s), 4.4–4.6 (2H, m), 4.2–4.4 (1H, m), 3.9–4.1 (1H, m), 3.8–4.0 (3H, s), 3.2–3.4 (2H, d), 1.0–1.2 (9H, s).

EXAMPLE 31

2-(2-Methoxyphenyl)-8-(1-methylpropyl)-5,6,7,8-tetrahydro-7-((thiazolidin-4-yl)carbonyl)-imidazo[1,2a]pyrazine (Compound 31)

Compound 31 was prepared in a manner analogous to example 18 except Boc-(L)-thiaproline was used for the coupling in step e. Mass spec. 401.3 (MH+). NMR (300

MHz, DMSO-d6, 90 C.) 8.0–8.2 (1H, d), 7.85–8.0 (1H, s), 7.3–7.5 (1H, t), 7.15–7.25 (1H, d), 7.05–7.15 (1H, t), 5.7–5.85 (1H, d), 4.75–5.0 (1H, s), 4.45–4.7 (1H, m), 4.3–4.45 (2H, m), 4.15–4.3 (2H, m), 3.9–4.0 (3H, s), 3.8–3.95 (1H, m), 3.4–3.6 (1H, t), 3.1–3.25 (1H, m), 2.25–2.45 (1H, m), 1.4–1.6 (1H, m), 1.15–1.4 (1H, m), 1.0–1.23 (3H, t), 0.8–1.0 3H, t).

Antiproliferative Activity of Farnesyl-transferase Inhibitors on Human Tumoral Cells The assays were performed using either A-427 lung carcinomas (expressing mutated Ki-ras gene), HT-29 colon adenocarcinomas (expressing wild type ras gene), Calu-1 lung carcinomas (expressing mutated Ki-ras gene), and MIA-PaCa pancreatic cancer cells (expressing mutated Ki-ras gene). These tumoral cells were seeded on 96 well plates at day 0 and maintained at 37° C. in 5% $CO_2$ atmosphere. At day 1, cells were treated with increased concentrations of test compounds ranging from 0 to 100 $\mu$M for 96 hrs. At the end of this period, the quantification of cell proliferation was evaluated by the colorimetric assay based on the cleavage of the tetrazolium salt WST-1 by mitochondrial dehydrogenases in viable cells leading to the formazan formation (Cell Proliferation Reagent WST-1 Kit, Boehringer Mannheim, Germany). These experiments, done in octuplicate, were repeated twice. The results, shown in Table I, depict the concentration range ($\mu$M) of test compound required to inhibit proliferation as compared to control cells in which no test compound was added.

TABLE I

| COMPOUND | CELL TYPE | | | |
| --- | --- | --- | --- | --- |
| | A-427 | HT-29 | Calu-1 | MIA PaCa-2 |
| 3 | 6.25–12.5 | 12.5 | 10–30 | 12.5–25 |
| 4 | 12.5–25 | 50–100 | 10–30 | |
| 5 | 6.25–25 | 50–100 | 12.5–25 | |
| 6 | | 50–100 | | |
| 8 | 12.5–25 | 25 · 50 | 25–50 | |
| 10 | 3.12–125 | 25–50 | 3–10 | |
| 11 | 6.25–12.25 | 50–100 | 30–100 | |
| 12 | 3.12–6.25 | 50 | 10–30 | |
| 13 | 6.25–12.5 | 25–50 | 12.5–50 | |
| 14 | 3.12–12.5 | 50–100 | 10–30 | |
| 15 | 6.25–12.5 | 25–50 | 12.5–25 | |
| 16 | 3.12–12.5 | 25–50 | 12.5–25 | |
| 17 | 6.25–12.5 | 6–12.5 | 12.5–25 | |
| 18 | 6.25 | 50–100 | 12.5–25 | |
| 19 | 0.78–1.56 | | 6.25–12.5 | |
| 20 | 0.78 | 50–100 | 6.25–12.5 | 12.5 |
| 21 | 12.5–25 | 25–50 | 25–50 | |
| 22 | 6.25–12.5 | | 12.5–25 | |
| 23 | 3.12–6.25 | 12.5–25 | 6.25–12.5 | |
| 24 | 6.25–12.5 | 50–100 | | 25–50 |
| 25 | 0.78–1.56 | 12.5–25 | 12.5–25 | 6.25–12.5 |
| 26 | 0.39–1.56 | 12.5 | 12.5–25 | 6.25–12.5 |
| 27 | 6.25 | 50–100 | 12.5–25 | |
| 28 | 12.5–25 | | 50–100 | |
| 29 | 3.12–6.25 | 25–50 | | 6.25–12.5 |
| 30 | 3.12–6.25 | 25–50 | | 12.5–25 |
| 31 | | 25–50 | | |

Other Embodiments

It is to be understood that while the invention has been described in conjunction with the detailed description thereof, that the foregoing description is intended to illustrate and not limit the scope of the invention, which is defined by the scope of the appended claims. Other aspects, advantages, and modifications are within the claims.

What is claimed is:
1. A compound having the formula (I):

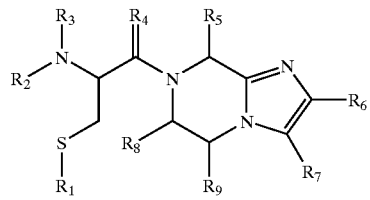

wherein:
$R_1$ is H;
$R_2$ is H;
$R_3$ is H;
$R_4$ is $H_2$ or O;
$R_6$ is phenyl, 1-naphthyl, or phenyl substituted with halo, lower alkyl or lower alkoxy;
$R_5$ is lower alkyl, cycloalkyl, or cycloalkyl lower alkyl;
$R_7$ is H;
$R_8$ is H;
$R_9$ is H;
or a pharmaceutically acceptable salt thereof.

2. A compound having the formula (I):

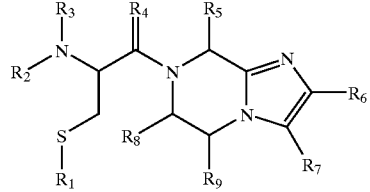

wherein:
$R_1$ is H;
$R_2$ is H;
$R_3$ is H;
$R_4$ is $H_2$ or O;
$R_6$ is H;
$R_7$ is phenyl, 1-naphthyl, or phenyl substituted or unsubstituted with halo, lower alkyl, or lower alkoxy;
$R_5$ is lower alkyl, cycloalkyl, or cycloalkyl lower alkyl;
$R_8$ is H;
$R_9$ is H;
or a pharmaceutically acceptable salt thereof.

3. A compound having the formula (I):

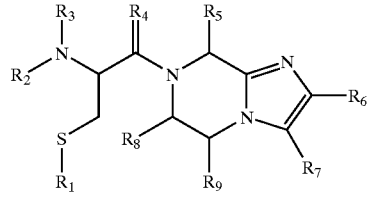

wherein:
$R_1$ is H;
$R_2$ is H;
$R_3$ is H;
$R_4$ is $H_2$ or O;

$R_5$ is lower alkyl, cycloalkyl, or cycloalkyl lower alkyl;

$R_6$ is phenyl, naphthyl, or phenyl substituted with halo, lower alkyl, or lower alkoxy;

$R_7$ is halo, phenyl, 1-naphthyl, or phenyl substituted with halo, lower alkyl, or lower alkoxy;

$R_8$ is H;

$R_9$ is H;

or a pharmaceutically acceptable salt thereof.

4. A compound of the formula S-(dimethylethyl)-S'-[2-amino-3-oxo-3(8-butyl-2-(2-methoxy-phenyl)-5,6,7,8-tetrahydroimidazo[1,2a]pyrazin-7-yl) propyl]disulfide, [S-[2-amino-3-oxo-3-(8-cyclohexylmethyl)-2-(2-methoxyphenyl)-5,6,7,8-tetrahydro-imidazo[1,2a]pyrazin-7-yl)-propyl]-S'-cyclohexyl]disulfide or [S-[2-amino-3-oxo-3-(8-cyclohexylmethyl)-2-(2-methoxyphenyl)-5,6,7,8-tetrahydro-imidazo[1,2a]pyrazin-7-yl)-propyl]-S'-ethyl]disulfide.

* * * * *